US007256708B2

(12) United States Patent
Rosenfeld et al.

(10) Patent No.: US 7,256,708 B2
(45) Date of Patent: *Aug. 14, 2007

(54) TELECOMMUNICATIONS NETWORK FOR REMOTE PATIENT MONITORING

(75) Inventors: Brian Rosenfeld, Baltimore, MD (US); Michael Breslow, Lutherville, MD (US)

(73) Assignee: VISICU, Inc., Baltimore, MD (US)

( * ) Notice: Subject to any disclaimer, the term of this patent is extended or adjusted under 35 U.S.C. 154(b) by 383 days.

This patent is subject to a terminal disclaimer.

(21) Appl. No.: 10/946,548

(22) Filed: Sep. 21, 2004

(65) Prior Publication Data

US 2006/0071797 A1    Apr. 6, 2006

Related U.S. Application Data

(63) Continuation-in-part of application No. 09/443,072, filed on Nov. 18, 1999, now Pat. No. 6,804,656.

(60) Provisional application No. 60/141,520, filed on Jun. 23, 1999.

(51) Int. Cl.
*G08C 19/16* (2006.01)
(52) U.S. Cl. ............... 340/870.01; 340/539.12; 340/539.18; 600/300; 705/3
(58) Field of Classification Search ............ 340/573.1
See application file for complete search history.

(56) References Cited

U.S. PATENT DOCUMENTS 3,646,606 A * 2/1972 Buxton et al. ............... 600/483
4,365,199 A   12/1982 McNair
4,489,387 A   12/1984 Lamb et al.

(Continued)

FOREIGN PATENT DOCUMENTS

WO    WO98/29790    7/1998

(Continued)

OTHER PUBLICATIONS

Grundy, Betty Lou; Jones, Paul; Lovitt, Ann; "Telemedicine in critical care: Problems in design, implementation and assessment" Jul. 1982. Critical Care Medicine vol. 10, No. 7.

(Continued)

*Primary Examiner*—Benjamin C. Lee
*Assistant Examiner*—Eric M. Blount
(74) *Attorney, Agent, or Firm*—Roberts Mardula & Wertheim, LLC

(57) ABSTRACT

A communications network for providing continuous patient monitoring to provide critical care services from a remote location. A plurality of patient monitoring stations with associated patient monitoring instrumentation is connected over a communications network to a command center to which data flows continuously for analysis. A standardized series of guideline algorithms for treating a variety of critical care conditions are prompted to provide critical care by caregivers who monitor the progress of individual patients at remote patient monitoring stations. A smart alert system that can be flexibly set from the command center provides for patient-specific rules to be established to alert the caregivers to potential patient problems so that intervention can occur in a timely fashion. A data storage/data warehouse function analyzes individual patient information from a plurality of command centers and provides updated algorithms and critical care support to the remote command centers.

89 Claims, 10 Drawing Sheets

U.S. PATENT DOCUMENTS

| | | |
|---|---|---|
| 4,731,725 A | 3/1988 | Suto et al. |
| 4,838,275 A | 6/1989 | Lee |
| 4,852,570 A | 8/1989 | Levine |
| 4,878,175 A | 10/1989 | Norden-Paul et al. |
| 5,255,187 A | 10/1993 | Sorensen |
| 5,321,800 A | 6/1994 | Lesser |
| 5,331,549 A * | 7/1994 | Crawford, Jr. ............... 600/513 |
| 5,348,008 A | 9/1994 | Bornn et al. |
| 5,416,695 A * | 5/1995 | Stutman et al. ............. 600/300 |
| 5,544,649 A * | 8/1996 | David et al. ................. 600/301 |
| 5,544,661 A | 8/1996 | Davis et al. |
| 5,574,828 A | 11/1996 | Hayward et al. |
| 5,576,952 A | 11/1996 | Stutman et al. |
| 5,619,991 A | 4/1997 | Sloane |
| 5,678,562 A | 10/1997 | Sellers |
| 5,701,894 A | 12/1997 | Cherry et al. |
| 5,715,449 A | 2/1998 | Peters, Jr. et al. |
| 5,724,580 A | 3/1998 | Levin et al. |
| 5,729,204 A | 3/1998 | Fackler et al. |
| 5,772,585 A | 6/1998 | Lavin |
| 5,812,983 A | 9/1998 | Kumagai |
| 5,822,544 A | 10/1998 | Chaco et al. |
| 5,823,948 A | 10/1998 | Ross, Jr. et al. |
| 5,832,450 A | 11/1998 | Myers et al. |
| 5,839,438 A | 11/1998 | Chen et al. |
| 5,842,978 A | 12/1998 | Levy |
| 5,855,550 A * | 1/1999 | Lai et al. ..................... 600/300 |
| 5,867,821 A | 2/1999 | Ballantyne et al. |
| 5,868,669 A | 2/1999 | Iliff |
| 5,899,855 A | 5/1999 | Brown |
| 5,924,074 A * | 7/1999 | Evans ........................... 705/3 |
| 5,942,986 A * | 8/1999 | Shabot et al. ............... 340/7.29 |
| 5,987,519 A * | 11/1999 | Peifer et al. ................. 709/230 |
| 6,024,699 A | 2/2000 | Surwit et al. |
| 6,093,146 A * | 7/2000 | Filangeri .................... 600/300 |
| 6,102,856 A | 8/2000 | Groff et al. |
| 6,139,494 A * | 10/2000 | Cairnes ....................... 600/300 |
| 6,154,668 A | 11/2000 | Pedersen et al. |
| 6,168,563 B1 * | 1/2001 | Brown ........................ 600/301 |
| 6,171,237 B1 * | 1/2001 | Avitall et al. ............... 600/300 |
| 6,215,403 B1 | 4/2001 | Chan et al. |
| 6,221,012 B1 * | 4/2001 | Maschke et al. ................ 705/3 |
| 6,225,901 B1 | 5/2001 | Kail, IV |
| 6,230,142 B1 | 5/2001 | Benigno et al. |
| 6,234,964 B1 | 5/2001 | Iliff |
| 6,238,338 B1 | 5/2001 | DeLuca et al. |
| 6,245,013 B1 | 6/2001 | Minoz et al. |
| 6,254,536 B1 | 7/2001 | Devito |
| 6,278,999 B1 | 8/2001 | Knapp |
| 6,292,698 B1 | 9/2001 | Duffin et al. |
| 6,304,788 B1 | 10/2001 | Eady et al. |
| 6,312,378 B1 * | 11/2001 | Bardy ......................... 600/300 |
| 6,315,719 B1 | 11/2001 | Rode et al. |
| 6,364,834 B1 * | 4/2002 | Reuss et al. ................. 600/300 |
| 6,385,589 B1 * | 5/2002 | Trusheim et al. ............... 705/2 |
| 6,398,728 B1 | 6/2002 | Bardy |
| 6,442,433 B1 | 8/2002 | Linberg |
| 6,533,724 B2 | 3/2003 | McNair |
| 6,551,243 B2 * | 4/2003 | Bocionek et al. ........... 600/300 |
| 6,741,264 B1 | 5/2004 | Lesser |
| 6,835,176 B2 | 12/2004 | McNair |
| 6,893,396 B2 | 5/2005 | Schulze et al. |
| 2002/0002473 A1 | 1/2002 | Schrier et al. |
| 2002/0177758 A1 | 11/2002 | Schoenberg et al. |
| 2002/0177759 A1 | 11/2002 | Schoenberg et al. |
| 2002/0187483 A1 | 12/2002 | Hoffman et al. |
| 2002/0193667 A1 | 12/2002 | McNair |
| 2003/0036687 A1 | 2/2003 | Schoenberg et al. |
| 2004/0030578 A1 | 2/2004 | Cross et al. |
| 2004/0063031 A1 | 4/2004 | Gallucci et al. |
| 2004/0078366 A1 | 4/2004 | Crooks et al. |
| 2004/0193451 A1 | 9/2004 | McNair |
| 2004/0197813 A1 | 10/2004 | Hoffman et al. |
| 2004/0199333 A1 | 10/2004 | Hoffman et al. |
| 2004/0225201 A1 | 11/2004 | McNair |
| 2004/0236604 A1 | 11/2004 | McNair |
| 2005/0027563 A1 | 2/2005 | Fackler et al. |
| 2005/0049891 A1 | 3/2005 | Wilson |
| 2005/0060191 A1 | 3/2005 | Parkins et al. |
| 2005/0075794 A1 | 4/2005 | Hoffman et al. |
| 2005/0075904 A1 | 4/2005 | Wagner et al. |
| 2005/0076060 A1 | 4/2005 | Finn et al. |
| 2005/0125098 A1 | 6/2005 | Wang et al. |
| 2005/0125256 A1 | 6/2005 | Schoenberg et al. |
| 2005/0206518 A1 | 9/2005 | Welch et al. |
| 2005/0228241 A1 | 10/2005 | McNair |
| 2005/0251418 A1 | 11/2005 | Fox, Jr. et al. |
| 2005/0267351 A1 | 12/2005 | Humphrey et al. |
| 2005/0283062 A1 | 12/2005 | Hoffman et al. |
| 2006/0031018 A1 | 2/2006 | Bush et al. |
| 2006/0036542 A1 | 2/2006 | McNair |

FOREIGN PATENT DOCUMENTS

| | | |
|---|---|---|
| WO | WO99/13766 | 3/1999 |

OTHER PUBLICATIONS

Editors: M. Michael Shabot and Reed M. Gardner, Computers and Medicine: Decision Support Systems in Critical Care, 1994, Springer-Verlag New York, Inc. New York.

Gilad J. Kuperman, M.D. and Reed M. Gardner, Ph.D., The Help System: A Snapshot in Time, 1988, Dept. of Biophysics, LDS Hospital, Salt Lake City, Utah.

Project Leaders: Benoit Dawant, Ph.D. and John A. Morris, Jr. M.D., Vanderbilt University Simon Project Website, 2004, Vanderbilt University, Nashville, Tennessee.

Greg Borzo, Web Technology: Coming Soon to a Hospital Near You, American Medical News, Nov. 18, 1996, American Medical Association www.amednews.com.

Abstract: J.E. Gray, C. Safran, R.B. Davis, G. Pomilio-Weitzner, J.E. Stewart, L. Zaccagnini and D. Pursley, Baby Care Link: Using the Internet and Telemedicine to Improve Care for High-risk Infants, Dec. 2000, Pediatrics, vol. 106, No. 6, pp. 1318-1324.

Abstract: Ray Duncan and Jeffrey J. Pomerance, Computer Assistance in Delivery of Patient Care in a Neonatal Intensive Care Unit, The Use of Computers in Perinatal Medicine, Chapter 19, pp. 337-351, 1982, Praeger Publishers, New York, NY.

Abstract: Ray Duncan, MD, Computer Assisted Care in the Neonatal Intensive Care Unit, Proceedings of the 17th Annual Symposium on Computer Applications in Medical Care, Nov. 1993, p. 929, American Medical Informatics Association.

Abstract: Metnitz PG, Laback P. Popow C, Laback 0, Lenz K, Hiesmayr M, Computer assisted data analysis in intensive care: the ICDEV project—development of a scientific database system for intensive care (Intensive Care Data Evaluation Project), International Journal of Clinical Monitoring and Computing, 1995, vol. 12, No. 3, pp. 147-159.

Abstract: Paul H. Peristein, MD, Neil K. Edwards, MS, Harry D. Atherton, MS, James M. Sutherland, MD, Computer Assisted Newborn Intensive Care, Pediatrics, Apr. 1976, vol. 57, No. 4, pp. 494-501.

Abstract: Edward H. Shortliffe, MD, Phd, Computer Programs to Support Clinical Decision Marking.

Tsien, C.L. and Fackler, J.C., "Poor prognosis for existing monitors in the intensive care unit," Critical Care Medical Journal, vol. 25, No. 4 (1997) (p. 614-619).

Tsien, C.L. "Reducing False Alarms in the Intensive Care Unit: A Systematic Comparison of Four Algorithms," Proceedings Annual AMIA Fall Symposium (1997).

Kohane, I.S. and Halmowitz, I.J., "Hypothesis-Driven Data Abstraction with Trend Templates," Proceedings Annual AMIA Symposium on Computer Applications in Medical Care (1994), (p. 444-448).

Terry Ann Capuano, et al., Remote Telemetry, Nursing Management, Vo. 26, No. 7, Jul. 1995, p. 26.

Valeriy Nenov and John Klopp, Remote Access to Neurosurgical ICU Physiological Data using the World Wide web, health Care in the Information Age, 1996, pp. 242-249.

Betty L. Grundy, et al., Telemedicine in Critical Care: An Experiment in Health Care Delivery, JACEP, vol. 6, Oct. 1977, pp. 439-444.

Susan L. Mabry, et al., Integrated Medical Analysis System, Proceedings of the 1997 Winter Simlation Conferece,, 1997, pp. 1167-1168.

Simon M. Kaplan and Geraldine Fitzpatrick, Designing Support for Remote Intensive-Care Telehealth Using the Locales Framework, ACM, 1997, pp. 173-184.

Douglas A. Perednia, Telemedine Technology and Clinical Applications, JAMA, vol. 6, Feb. 8, 1995, p.

Silvia Miksch,Artificial Intelligence for Decision Support: Needs, Possibilities, and Limitations in ICU, 10th Postgraduate Cousre in Critical Care Medicine A.P.I.C.E. '95, Springer 1995 pp. 1-11.

Silvia Miksch, Artificial Intelligence for Decision Support: Needs Possibilities, and Limitations in ICU, 10th Postgraduate Course in Critical Care Medicine APICE '95, Springer, 1995.

Doctors use 'remote control' to monitor ICU patients, CNN.com. technology>computing, Aug. 21, 2000, http://www.cnn.com/2000/TECH/computing/08/21/icu.t_t/.

Finding Value in Intensive Care, From Afar, The New York Times on the Web, Jul. 27, 1999, www.Visicu.com/companynews/0799_nytimes.htm.

Remote Monitoring of ICU Patients Lowers Mortality Rates, Complications, Johns Hopkins Newsrelease, Mar. 20, 2001, http://www.newswise.com/areticles/2001/3/ICU.JHM.html.

Brian A. Rosenfeld, M.D., FCCM, FCCP, et al., Intensive care unit telemedicine: Alternate paradigm for providing continuous intensivist care, Critical Care Medicine, vol. 28, No. 12, 2000 p. 3925.

Guidelines for Intensive Care Unit Design, Critical Care Medicine, Mar. 1995; 23(3):582-588.

Michael Breslow, et al., Effect of a Multiple-Site Intensive Care Unit Telemedicine Program on clinical and Economic Outcomes: An Alternative Paradigm for Intensivist Staffing, Critical Care Medicine 2004 vol. 32, No. 1.

Richard Brilli, et al., Critical care Delivery in the Intensive Care Unit: Defining Clinical Roles and the Best Practice Model, Critical Care Medicine 2001 vol. 29, No. 10.

M. Michael Shabot, et al., Decision Support Systems in Critical Care, 1994, Springer-Verlag Publishing, New York.

Rosenfeld, et al. Intensive care unit telemedicine: alternate paradigm for providing continuous intensivist care, Dec. 28, 2000, www.ncbi.nlm.nih.gov.

Definitions of Intensive Care Unit (ICU) on the Web, Apr. 2004, www.google.com and other websites.

Abstract: Paul H. Peristein, MD, Neil K. Edwards, MS, Harry D. Atherton, MS, James M. Sutherland, MD, Computer Assisted Newborn Intensive Care, Pediatrics, Apr. 1976, vol. 57, No. 4, pp. 494-501.

Abstract: Merz U, Peschgens T. Budde R, Kretzschmann F, Homchen H V, Computer-assisted monitoring in the neonatal intensive care unit [German], Klin Padiatr, Nov./Dec. 1995, vol. 207, No. 6, pp. 331-333.

Abstract: Charles Safran, MD, Francois Herrman, MD, David Rind, MD, Hollis B. Kowaloff, BA, Howard L. Bleich, MD, and Warner V. Slack, MD, Computer-Based Support for Clinical Decision Making, M.D. Computing 1990, vol. 7, No. 5, pp. 319-322.

Abstract: Reed M. Gardner, PHD, Computerized Mangement of Intensive Care Patients, M.D. Computing, 1986, vol. 3, No. 1, pp. 36-51.

Abstract: F. John Lewis; Steven Deller; Michael Quinn; Benjamin Lee; Raymond Will; and John Raines, Continuous Patient Monitoring with a Small Digital Computer, Computers and Biomedical Research, 1972, vol. 5, pp. 411-428.

Abstract: N. Fumai, C. Collet, M. Petroni, K. Roger, A. Lam, E. Saab, A.'S. Malowany, F. A. Carnevale, R. D. Gottesman, Database Design of an Intensive Care Unit Patient Data Management System, Proceedings of the Fourth Annual IEEE Symposium on Computer-Based Medical Systems, May 12, 1991, pp. 78-85, IEEE Computer Society Press, Los Alamitos, CA.

Abstract: George Hripcsak; Paul D. Clayton; Robert A. Jenders; James J. Cimino; and Stephen B. Johnson, Design of a Clinical Event Monitor, Computers and Biomedical Research, Jun. 1996, vol. 29, No. 3, pp. 194-221.

Abstract: David M. Rind, MD; Roger Davis, SCD; and Charles Safran, MD, Designing Studies of Computer-Based Alerts and Reminders, MD Computing, 1995, vol. 12, No. 2, pp. 122-126.

Abstract: Dwayne R. Westenkow, PHD, Automating Patient Care with Close-Loop Control, M.D. Computing, 1986, vol. 3, No. 2, pp. 14-20.

Abstract: Snowden S, Brownlee KG, Dear P R, An expert system to assist neonatal intensive care, I Med Eng Technol Mar.-Apr. 1997;21(2):67-73, vol. 21, No. 2, pp. 67-73.

Abstract: A. Airfredo Morales, Engr., MS, James Gray, MD, MS , Charles Safran, MD, An Application Server Approach for Integration of Clinical Systems, Proceedings of the AMIA 1999 Annual Symposium, 1999, AMIA.

Abstract: Kang Wang, PHD; Isaac Kohane, MD, PHD; Karen L. Bradshaw, BS; James Facider, MD, A Real Time Patient Monitoring System on the World Wide Web, Proceedings of the 1996 AMIA Annual Fall Symposium, Nov. 1996, pp. 729-732, Hanley and Belfus, Inc.

Abstract: Michael Factor, David H. Gelernter, Craig E. Kolb, Perry L. Miller and Dean F. Sittig, Real-Time Data Fusion in the Intensive Care Unit, IEEE Comuter, Nov. 1991, pp. 45-53.

Editor: Judy G. Ozbolt, Ph.D., A Conference of the American Medical Informatics Association, Symposium on Computer Applications in Medical Care, Nov. 5-9, 1994, Hanley & Belfus, Inc. Medical Publishers, Philadelphia, PA.

W. Hsueh-Fen Young, Reed M. Gardner, Thomas D. East and Kristi Turner, Computerized Ventilator Data Selction: Artifact Rejection and Data Reduction, Int'l Journal of Clinical Monitoring and Computing 1997, 14: 165-176, Kluwer Academic Publishers, Netherlands.

Randolph A. Miller, M.D. and Reed M. Gardner, Ph.D., Summary Recommendations for Responsible Monitoring and Regulation of Clinical Software Systems, Annals of Internal Medicine, Nov. 1997, vol. 127, No. 9.

Reed M. Gardner, T. Allan Pryor and Homer R. Warner, The HELP Hospital Information System: Update 1998, Intl Journal of Medical Informatics 1999, vol. 54, pp. 169-182, Elsevier Science Ireland Ltd., Ireland.

Martin Spikoff, Systems Aid Rural Health Delivery, QIPhysician. com, Sep. 2003.

Abstract: Jerome P. Kassirer, MD, The Next Transformation in the Delivery of Health Care (Editorial), NEJM, Jan. 5, 1995, vol. 332, No. 1, pp. 52-54.

Abstract: Lorene S. Avila; M. Michael Shabot, Keys to the successful implementation of an ICU patient data management system, International Journal of Clinical Monitoring and Computing, 1988, vol. 5, pp. 15-25.

Abstract: Reed M. Gardner, MD; M. Michael Shabot, MD, Computerized ICU Data Mangement: Pitfalls and Promises, International Journal of Clinical Monitoring and Computing, 1990, vol. 7, pp. 99-105.

Karl W. Thomas, M.D., Charles S. Dayton, B.S., R.Ph., and Michael W. Peterson, M.D., Evolution of Internet-Based Clinical Decision Support Systems, Journal of Medical Internet Research 1999, vol. 1, University of Iowa, Iowa City, Iowa.

Abstract: C. J. McDonald, Protocol-Based Computer Reminders, The Quality of Care and The Non-Perfectability of Man, The New England Journal of Medicine, Dec. 9, 1976, vol. 295, No. 24, 1351-1355.

Abstract: T.D. East, A.H. Morris, C.J. Wallace, T.P. Clemmer, J.F. Orme, Jr., L.K. Weaver, S. Henderson and D.F. Sittig, A Strategy for Development of Computerized Critical Care Decision Support Systems, Intl Journal of Clinical Monitoring and Computing, 1991-92, vol. 8, No. 4, 263-269.

Dr. Ramana Reddy and Dr. V. "Juggy" Jagannathan, Secure Collaboration Technology for Rural Clinical Telemedicine, National Library of Medicine, Oct. 8, 1996 Press Release, West Virginia University, West Virginia.

Martin J. Tobin, M.D., Principles and Practice of Intensive Care Monitoring, 1998, McGraw-Hill Inc.

Peter J. Haug, Reed M. Gardner, and R. Scott Evans, "Hospital-Based Decision Support" in *Clinical Decision Support Systems: Theory and Practice*, ETA S. Berner [ed.], 1999, Springer-Verlag New York, Inc., New York, NY, pp. 77-103.

Clement J. McDonald, M.D. and William M. Tierney, M.D., Computer-Stored Medical Records: Their Future Role in Medical Practice, JAMA, Jun. 17, 1988, pp. 3433-3440, vol. 259, No. 23.

Gilad J. Kuperman, Reed M. Gardner, and T. Allan Pryor, Help: A Dynamic Hospital Information System, 1991, Springer-Verlag New York, Inc., New York, NY.

Dickey Seidlitz Johnson, Jane Ranzenberger, Ruth D. Herbert, Reed M. Gardner, and Terry P. Clemmer, A Computerized Alert Program for Acutely Ill Patients, Journal of Nursing Administration, Jun. 1980, pp. 26-35.

Reed M. Gardner, Ph.D., Blair J. West, M.S., T. Allan Pryor, Ph.D., Keith G Larsen, R.Ph., Homer R Warner, M.D., Terry P Clemmer, M.D., James F. Orme, Jr. M.D., Computer-Based ICU Data Acquisition as an Aid to Clinical Decision-Making, Critical Care Medicine, 1982, pp. 823-830, vol. 10, No. 12, The Williams & Wilkins Co.

Reed M. Gardner and Terry P. Clemmer, Computerized Protocols Applied to Acute Patient Care, 1977, Mediad Inc., Tarrytown, NY.

Karen E. Bradshaw, Reed M. Gardner, and T. Allan Pryor, Development of a Computerized Laboratory Alerting System, Computers and Biomedical Research 22, 575-587, 1989, Academic Press, Inc.

Terry P. Clemmer and Reed M. Gardner, Medical Informatics in the Intensive Care Unit: State of the Art 1991, International Journal of Clinical Monitoring and Computing 8: 237-250, 1992, Kluwer Academic Publishers, Netherlands.

Reed M. Gardner, Ph.D., David V. Ostler, and O. Hank Duffy, M.D., Computers in the Emergency Room, Internal Medicine for the Specialist, vol. 8, No. 3, Mar. 1987.

Dean F. Sittig, Nathan L. Pace, Reed M. Gardner, Eduardo Beck, and Alan H. Morris, Implementation of a Computerized Patient Advice System Using the HELP Clinical Information System, Computers and Biomedical Research 22, 474-487, 1989, Academic Press Inc.

P. D. Clayton, R. Scott Evans, T. Pryor, R. M. Gardner, P. J. Haug, O. B. Wigertz, and H. R. Warner, Bringing HELP to the Clinical Laboratory—Use of an Expert System to Provide Automatic Interpretation of Laboratory Data, Ann Clin Biochem 1987; 24: Supplement.

D. F. Sittig, Ph.D., R. M. Gardner, Ph.D., N. L. Pace, M.D., M. Bombino, M. D., and A. H. Morris, M.D., Compas: A Computerized Patient Advice System to Direct Ventilatory Care, Medical Informatics 88: Computers in Clinical Medicine, Sep. 13-15, 1988, British Medical Informatics Society, London.

Karen E. Bradshaw, Ph.D., Dean F. Sittig, Ph.D., Reed M. Gardner, Ph.D., T. Alllan Pryor, Ph.D., and Marge Budd, M.S., Improving Efficiency and Quality in a Computerized ICU, 1988 SCAMC, Inc.

Dean F. Sittig, Ph.D., C. Gregory Elliott, M.D., C. Jane Wallace, R.N., B.S.N., Polly Bailey, R.N., Reed M. Gardner, Ph.D., Computerized Screening for Identification of Adult Respiration Distress Syndrome (ARDS) Patients, 1988 SCAMC, Inc.

R. Scott Evans, Ph.D., Reed M. Gardner, Ph.D., John P. Burke, M.D., Stanley L. Pestotnik, R.P.H., Robert A. Larsen, M.D., David C. Classen, M.D., and Paul D. Clayton, Ph.D., A Computerized Approach to Monitor Prophylactic Antibiotics, 1987, SCAMC, Inc.

C. Gregory Elliott, M.D., Deon Simmons, R.R.T., C. Duwayne Schmidt, M.D., Kip Enger, B.S., C.R.T.T., Loren Greenway, B.S., R.R.T., and Reed M. Gardner, Ph.D., Computer-Assisted Medical Direction of Respiratory Care, Respiratory Management, vol. 19, No. 2.

H. Keller and CH. Trendelenburg, Data Presentation Interpretation, Clinical Biochemistry Principles, Methods, Applications, Walter-deGruyter & Co., 1989.

Reed M. Gardner, Ph.D., Karen W. Hollingsworth, R.N., M.S, C.C.R.N., ECG and Pressure Monitoring: How to Obtain Optimal Results, 295-305.

Emmanuel Furst, Ph.D., Cardiovascular Technology, The Journal of Cardiovascular Nursing, Nov. 1989, 68-78.

Dean F. Sittig, Reed M. Gardner, Nathan L. Pace, Alan H. Morris, and Eduardo Beck, Computerized Management of Patient Care in a Complex, Controlled Clinical Trial in the Intensive Care Unit, Computer Methods and Programs in Biomedicine 30, 1989, 77-84.

Karen E. Bradshaw, Ph.D., Dean F. Sittig, Ph.D., Reed M. Gardner, Ph.D., T. Allan Pryor, Ph.D., and Marge Budd, R.N., M.S., Computer-Based Data Entry for Nurses in the ICU, Clinical Computing, Nov. 1988.

Thomas D. East, Ph.D., Alan H. Morris, M.D., Terry Clemmer, M.D., James F. Orme, M.D., C. Jane Wallace, B.S.N., Susan Henderson, B.A., Dean F. Sittig, Ph.D., Reed M. Gardner, Ph.D., Development of Computerized Critical Care Protocols—A Strategy That Really Works!, 1990 LDS Hospital, Salt Lake City, UT.

R. Scott Evans, Ph.D., John P. Burke, M.D., Stanley L. Pestonik, R.Ph., David C. Classen, M.D., Ronald L. Menlove, Ph.D., and Reed M. Gardner, Ph.D., Prediction of Hospital Inflections and Selection of Antibiotics Using an Automated Hospital Database, 1990, SCAMC, Inc. 663-667.

Susan E. Henderson, B.A., Robert O. Crapo, M.D., Thomas D. East, Ph.D., Alan H. Morris, M.D., C. Jane Wallace, R.N., Reed M. Gardner, Ph.D., Computerized Clinical Protocols in an Intensive Care Unit: How Well are They Followed?, 1990, SCAMC, Inc., LDS Hospital, Salt Lake City, UT.

Reed M. Gardner, PHD, Russell K. Hulse, RPH, MBA, Keith G. Larsen, RPH, Assessing The Effectiveness Of A Computerized Pharmacy System, 1990, SCAMC, Inc., 668-672.

Reed M. Gardner, "Patient-Monitoring Systems", *Medical Informatics: Computer Applications in Health Care*, E.H. Shortliffe and L.E. Perrealt (eds.), G. Wiederhold and L.M. Fagan (assoc. eds.) (Reading, MA: Addison-Wesley, 1990.

Reed M. Gardner, Olaf K. Golubjatnikov, R. Myron Laub, Julie T. Jacobson, and R. Scott Evans, Computer-Critiqued Blood Ordering Using the HELP System, Computers and Biomedical Research 23, 514-528, 1990, Academic Press, Inc.

Karen E. Tate, PH.D., Reed M. Gard'ner, PH.D., and Lindell K. Weaver, M.D., A Computerized Laboratory Alerting System, Clinical Computing, 1990, vol. 7, No. 5, 296-301.

Dean F. Sittig, Reed M. Gardner, Alan H. Morris, and C. Jane Wallace, Clinical Evaluation of Computer-Based Respiratory Care Algorithms, International Journal of Clinical Monitoring and Computing 7, 1990, 177-185, Kluwer Academic Publishers, Netherlands.

R. Scott Evans, Stanley L. Pestotnilc, John P. Burke, Reed M. Gardner, Robert A. Larsen, and David C. Classen, Reducing Tile Duration Of Prophylactic Antibiotic Use Through Computer Monitoring Of Surgical Patients, DICP, The Annals of Pharmacotherapy, Apr. 1990, vol. 24, 351-354, Harvey Whitney Books Company, Cincinnati, OH.

Reed M. Gardner, and M. Michael Shabot, Computerized ICU Data Management: Pitfalls and Promises, International Journal of Clinical Monitoring and Computing 7: 99-105, 1990, Kluwer Academic Publishers, Netherlands.

Stanley L. Pestotnik, R.PH., R. Scott Evans, PH.D., John P. Burke, M.D., Reed M. Gardner, PH.D., David C. Classen, M.D., Therapeutic Antibiotic Monitoring: Surveillance Using a Computerized Expert System, The American Journal of Medicine, Jan. 1990, vol. 88, 43-48.

Gil Kuperman, MD, Brent James, MD, Mstat, Julie Jacobsen, MT (ASCP), Reed M. Gardner, PHD, Continuous Quality Improvement Applied To Medical Care: Experiences At LDS Hospital, Medical Decision Making, Oct.-Dec. 1991, 60-65, vol. 11, No. 4.

Susan Henderson, Robert O. Crapo, C. Jane Wallace, Thomas D. East, Alan H. Morris, & Reed M. Gardner, Performance Of Computerized Protocols For The Management Of Arterial Oxygenation In An Intensive Care Unit, International Journal of Clinical Monitoring and Computing 8, 1992, 271-180, Kluwer Academic Publishers, Netherlands.

Eric F. Lepage, MD, Reed M. Gardner, PHD, R. Myron Laub, MD, Julie T. Jacobson, MT(ASCP), Assessing The Effectiveness Of A Computerized Blood Order Consultation' System, LDS Hospital, 1992, 33-37, AMIA, Inc.

E. Lepage, R. Traineau, PH. Marchetti, M. Benbunan, R. M. Gardner, Development Of A Computerized Knowledge Based System Integrated To A Medical Workstation: Application To Blood Transfusion, MEDINFO, 1992, 585-590, Elsevier Science Publishers B.V.

Reed M. Gardner, Ph.D., and R. Scott Evans, Ph.D., Computer-Assisted Quality Assurance, Group Practice Journal, May/Jun. 1992, 41(3), 8-11.

Thomas D. East, Ph.D., W. Hsueh-Fen Young, M.S., and Reed M. Gardner, Ph.D., Digital Electronic Communication between ICU Ventilators and Computers and Printers, Respiratory Care, Sep. 1992, vol. 37 No. 9, 1113-1123.

Reed M. Gardner, Computers in Critical Care, Wellcome Trends in Hospital Pharmacy, Jul. 1992.

T. Allan Pryor, Reed M. Gardner and W. Clinton Day, Computer System for Research and Clinical Application to Medicine, AFIPS—Conference Proceedings, vol. 33, 1968, 809-816.

Homer R. Warner, M.D., Reed M. Gardner and Alan F. Toronto, M.D., Computer-Based Monitoring of Cardiovascular Functions in Postoperative Patients, Supplement II to Circulation, Apr. 1968, vols. 37 & 38, 68-74.

Russell M. Nelson, Homer R. Warner, Reed E. Gardner and J. D. Mortensen, Comuter Based Monitoring of Patients Following Cardiac Surgery, Computers in Cardiology, Jul.-Aug. 1969, vol. 5, No. 4, 926-930.

Reed M. Gardner, Computerized Patient Monitoring at LDS Hospital—An Evaluation, Proceedings of the San Diego Biomedical Symposium, 1971, vol. 10, 151-159.

Reed M. Gardner, Monitoring of Physiological Data in a Clinical Environment, Annual Review of Biophysics and Bioengineering, 1972, vol. 1, 211-224.

Reed M. Gardner, Donald R. Bennet, and Richard B Vorce, Eight-Channel Data Set for Clinical EEG Transmission Over Dial-Up Telephone Network, IEEE Transactions on Biomedical Engineering, May 1974, vol. BME-21, No. 3, 246-249.

Reed M. Gardner, George H. Cannon, Alan H. Morris, Kenneth R. Olsen, W. Gary Price, Computerized Blood Gas Interpretation and Reporting System, Computer Magazine, Jan. 1975, 39-45.

Russell K. Hulse, Stephen J. Clark, J. Craig Jackson, Homer R. Warner and Reed M. Gardner, Computerized Medication Monitoring System, American Journal of Hospital Pharmacy 33, Oct. 1976, 1061-1064.

Reed M. Gardner, Ph.D., Computers in the ICU, Medical Electronics, Jun. 1984, 129-135.

Robert D. Andrews, M.S., M.T., Reed M. Gardner, Ph.D., Sandy M. Metcalf, R.R.T., and Deon Simmons, R.R.T., Computer Charting: An Evaluation of a Respiratory Care Computer System, Respiratory Care, Aug. 1985, vol. 30, No. 8, 695-707.

Reed M. Gardner, Ph.D., Computerized Data Management and Decision Making in Critical Care, Symposium on Critical Care, Aug. 1985, vol. 65, No. 4, 1041-1051.

Reed M. Gardner, David P. Scoville, Blair J. West, Beth Bateman, Robert M. Cundick, Jr., Terry P. Clemmer, Integrated Computer Systems for Monitoring of the Critically Ill, 1977, 301-307.

T. Allan Pryor, Reed M. Gardner, Paul D. Clayton, Homer R. Warner, A Distributed Processing System for Patient Management, Computers in Cardiology, Sep. 1978, 325-328.

Reed M. Gardner, Ph.D., Terry P. Clemmer, M.D., Keith G. Larsen, R.Ph., and Dickey S. Johnson, R.N., Computerized Alert System Use in Clinical Medicine, IEEE Session 6, 1979, 136-140.

T. P. Clemmer, R. M. Gardner, J. F. Orme, Jr., Computer Support in Critical Care Medicine, 1980.

Scott R. Cannon, and Reed M. Gardner, Experience with a Computerized Interactive Protocol System Using HELP, Computers and Biomedical Research 13, 1980, 399-409, Academic Press, Inc.

T. Allan Pryor, Paul D. Clayton, Reed M. Gardner, Randy Waki, and Homer R. Warner, HELP—A Hospital-Wide System for Computer-Based Support of Decision-Making, Jan. 1981.

T. A. Pryor, R. M. Gardner, P. D. Clayton and H. R. Warner, The HELP System, Proceedings of the Sixth Annual Symposium on Computer Applications in Medical Care, Oct.-Nov. 1982, 19-27, IEEE.

Reed M. Gardner, Information Management—Hemodynamic Monitoring, Seminars in Anesthesia, Dec. 1983, vol. 2, No. 4, 287-299.

T. A. Pryor, R. M. Gardner, P. D. Clayton, H. R. Warner, The HELP System, Journal of Medical Systems, 1983, vol. 7, No. 2, 87-102.

Reed M. Gardner, Blair J. West, T. Allan Pryor, Distributed Data Base and Network for ICU Monitoring, IEEE Computers in Cardiology, Sep. 18-24, 1984, 305-307.

Reed M. Gardner, T. Allan Pryor, Paul D. Clayton, and R. Scott Evans, Integrated Computer Network for Acute Patient Care, Symposium on Computer Applications in Medical Care, Nov. 4-7, 1984.

Reed M. Gardner, Tomorrow's Electronic Hospital is Here Today, IEEE Spectrum, Jun. 1984, 101-103.

Karen E. Bradshaw, Reed M. Gardner, Terry P. Clemmer, Jams F. Orme, Frank Thomas, and Blair J. West, Physician Decision Making—Evaluation of Data Used in a Computerized ICU, International Journal of Clinical Monitoring and Computing 1, 1984, 81-91.

Terry P. Clemmer, M.D., and Reed M. Gardner, Ph.D., Data Gathering, Analysis, and Display in Critical Care Medicine, Respiratory Care, Jul. 1985, vol. 30, No. 7, 586-601.

Reed M. Gardner, Ph.D., and William L. Hawley, Standardizing Communications and Networks in the ICU, Patient Monitoring and Data Management, 1985, 59-63.

R. Scott Evans, Reed M. Gardner, Allan R. Bush, John P. Burke, Jay A. Jacobsen, Robert A. Larsen, Fred A. Meier, and Homer R. Warner, Development of a Computerized Infectious Disease Monitor (CIDM), Computers and Biomedical Research 18, 1985, 103-113.

R. Scott Evans, PHD, Robert A. Larsen, MD, John P. Burke, MD, Reed M. Gardner, PHD, Frederick A. Meier, MD, Jay A. Jacobson, MD, Marlyn T, Conti, BSN, Julie T. Jacobson, MT, Russell K. Hulse, RPH, Computer Surveillance of Hospital-Acquired Infections and Antibiotic Use, Journal of the American Medical Association, Aug. 22-29, 1986, vol. 256, No. 8, 1007-1011.

Reed M. Gardner, Computerized Management of Intensive Care Patients, Images, Signals, and Devices, 1986, vol. 3, No. 1.

R. Whiting, L. Hayes, The Practice of Telemedicine—The TARDIS Perspective, Informatics in Healthcare—Australia, Jul./Aug. 1997, vol. 6, No. 3, 103-106.

Ho Sung Lee, Seung Hun Park, and Eung Je Woo, Remote Patient Monitoring Service Through World-Wide Web, Proceedings—19[th]International Conference—IEEE/EMBS, Oct. 30-Nov. 2, 1997, 928-931.

Betty L. Grundy, M.D., Pauline Crawford, R.N., Paul K. Jones, Ph.D., May Lou Kiley, Ph.D., Arnold Reisman, Ph.D., Yoh-Han Pao, Ph.D., Edward L. Wilkerson, M.D., J. S. Gravenstein, M.D., Telemedicine in Critical Care: An Experiment in Health Care Delivery, Oct. 1977, 6:10.

Betty Lou Grundy, M.D., Paul K. Jones, Ph.D., and Ann Lovitt, M.D., Telemedicine in Critical Care: Problems in Design, Implementation, and Assessment, Critical Care Medicine, Jul. 1982, vol. 10, No. 7, 471-475.

Geraldine Fitzpatrick, TARDIS Evaluation: Report on Final Usage Evaluation of the TARDIS Telehealth System, Jul. 24, 1998, Issue No. 1.0.

Xin Li, Daniel J. Valentino, George J. So, Robert Lufkin, Ricky K. Taira, A World Wide Web Telemedicine System, SPIE vol. 2711, 427-439.

Stephen M. Ayres, M.D., F.C.C.M., AKE Grenvik, M.D., Ph.D., F.C.C.M., Peter R. Holbrook, M.D., F.C.C.M., William C. Shoemaker, M.D., F.C.C.M., Textbook of Critical Care, 3rd Edition, 1995, Harcourt Brace & Company.

Karen B. Tate, PH.D., Reed M. Gardner, PH.D., Kurt Scherting, Nurses, Pagers, and Patient-Specific Criteria; Three Keys to Improved Critical Value Reporting, 1995, 164-168, AMIA, Inc.

Karen E. Tate, Ph.D., Reed M. Gardner, Ph.D., Computers, Quality, and the Clinical Laboratory: A Look at Critical Value Reporting, 17th Annual Symposium on Computer Applications in Medical Care, Oct. 30-Nov. 3, 1993, 193-197.

Peter J. Haug, Reed M. Gardner, Karen E. Tate, R. Scott Evans, Thomas D. East, Gilad Kuperman, T. Allan Pryor, Stanley M. Huff, and Homer R. Warner, Decision Support in Medicine: Examples from the HELP System, Computers and Biomedical Research 27, 1994, 396-418.

Thomas D. East, Ph.D., C. Jane Wallace, R.N., M.S., Alan H. Morris, M.D., Reed M. Gardner, Ph.D., and Dwayne R. Westenskow, Ph.D., Computers in Critical Care, New Technologies in Critical Care, Jun. 1995, vol. 7, No. 2, 203-216.

Reed M. Gardner, Ph.D., Bette B. Maack, R.R.A., R. Scott Evans, Ph.D., and Stanley M. Huff, M.D., Computerized Medical Care: The HELP System at LDS Hospital, Journal of AHIMA, Jun. 1992, 63(6):68-78.

Reed M. Gardner, Ph.D., Integrated Computerized Records Provide Improved Quality of Care with Little Loss of Privacy, Journal of the AMIA, Jul./Aug. 1994, vol. 1, No. 4, 320-322.

S Reddy, M Niewiadomska-Bugaj, Y V Reddy, H C Galfalvy, V Jagannathan, R Raman, K. Srinivas, R. Shank, T. Davis, S. Friedman, MD, B. Merkin, MD, M. Kilkenny,MD, Experience with ARTEMIS—An Internet-Based Telemedicine System, AMIA, 1997, 759-763.

Patrick R. Norris, M.S., Benoit M Dawant, Ph.D., Antoine Geissbuhler, M.D., Web-Based Data Integration and Annotation in the Intensive Care Unit, 1997.

H. C. Galfalvy, M.S., S. M. Reddy, Ph.D., M. Niewiadomska-Bugaj, Ph.D., S. Friedman, M.D., Evaluation of Community Care Network (CNN) System in a Rural Health Care Setting, 1995, AMIA Inc., 698-702.

K. Major, M. Shabot, S. Cunneen, Wireless Critical Alerts and Patient Outcomes in the Surgical Intensive Care Unit; The American Surgeon, 2000; p. 1057-1060.

M. Shabot, M. Lobue, Cedars-Sinai Medical Center Critical Alerting System, Feb. 2004; p. 1-16.

Shabot MM, LoBue M, Leyerle BJ, Dubin SB. Inferencing strategies for automated ALERTS on critically abnormal laboratory and blood gas data, SCAMC 1989; 13:54-57.

APACE® III Equation Update (Version III-J) 2002, pp. 1-22.

APACHE® III Equation Update (Version III-I) 2003, pp. 1-13.

O. Kostopoulau, M. Wildman, Sources of Variability in Uncertain Medical Decisions In the ICU: A Process Tracing Study, Qual. Saf. Health Care 2004, 13:272-280.

A. Seiver, Critical Care Computing: Past, Present, and Future: Critical Care Clinics, vol. 16, No. 4, Oct. 2000, p. 1-17.

J. Fisher, S. Harbarth, A. Agthe, A. Benn, S. Ringer, D. Goldmann, and S. Fancani, Quantifying Uncertainty: Physicians' Estimates of Infection in Critically Ill Neonates and Children; Clinical Infection Diseases 2004:38, pp. 1383-1390.

N. Halpern, S. Pastores, R. Greenstein, Critical Care Medicine in the United States 1985-2000: An Analysis of Bed Numbers, Use, and Cost; Critical Care Medicine 2004, vol. 32, No. 6, pp. 1254-1259.

J.Mrus, Getting Beyond Diagnostic Accuracy: Moving Toward Approaches That Can Be Used in Practice; Clinical Infectious Diseases 2004:38, pp. 1391-1393.

B. Leyerle, M. Shabot, Integrated Computerized Databases for Medial Data Management Beyond the Bedside, International Journal of Clinical Monitoring and Clinical Computing 1990:7, pp. 83-89.

M.Shabot, M. Lobue, B. Leyerle, S. Dubin, Decision Support Alerts For Clinical Laboratory and Blood Gas Data, Int. J. Clinical Monitoring and Computing 1990:7, pp. 27-31.

M. Shabot, M. Lobue, Real-Time Wireless Decision Support Alerts on a Palmtop PDA; Proc. Ann. Symp. Compt Appl. Med Care 1995, pp. 174-179.

W. Bates, M. Cohen, L. Leape, J. Overhage, M. Shabot, T. Sheridan, Reducing the Frequency of Errors In Medicine, J. American Medical Informatics Assn. 2001:8 pp. 299-308.

M. Shabot, B. Leyerle, M. Lobue, Automatic Extraction of Intensity Intervention Scores From A Computerized Surgical ICU Flowsheet, Am. J. Surg 1987:154:1, pp. 72-76.

Hetherington, Laurel Traynowicz; "High tech meets high touch: telemedicine's contribution to patient wellness"; Spring, 1998; Nursing Administration Quarterly, vol. 22, No. 3.

Tsien, Christine L., "TrendFinder: Automated Detection of Alarmable Trends", Department of Electrical Engineering and Computer Science, Massachusetts; Jun. 2000.

Hosseinzadeh, Abolfazl, "A Rule-Based System for Vital Sign Monitoring in Intensice Care", Department of Electrical Engineering, McGill University, Montreal; Nov. 1993.

Aukburg, S. J. et al., "Automation of Physiological Data Presentation and Alarms in the Post Anesthesia Care Unit." In Symposium on Computer Applications in Medical Care, Nov. 5-8, 1989, Washington, DC; pp. 580-582.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Bierman, M. l. et al., "Pulse Oximetry in the Postoperative Care of Cardiac Surgical Patients; A Randomized Controlled Trial." *Chest*, vol. 102, No. 5, Nov. 1992: 1367-1370.

Bradshaw, K. E., "Computerized Alerting System Warns of Life-Threatening Events." In Symposium on Computer Application in Medical Care, Oct. 25-26, 1986, Washington, DC; pp. 403-409.

Chizeck, H. J., "Modeling, Simulation and Control in a Data Rich Environment." In Symposium on Computer Applications in Medical Care, Oct. 25-26, 1986, Washington, DC; pp. 65-69.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia, Vol.* 3, No. 1, Feb. 1989: pp. 10-15.

Coplin, W. M. et al., "Accuracy of Continuous Jugular Bulb Oximetry in the Intensive Care Unit." Neurosurgery, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Guedes de Oliveira, P. et al., "The Role of Computer Based Techniques in Patient Monitoring: Technical Note." *Acta Neuorchir*, vol. 55, 1992 (Suppl.): 18-20.

Hahnel, J. et al., "Can a Clinician Predict the Technical Equipment a Patient will Need During Intensive Care Unit Treatment? An Approach to Standardize and Redesign the Intensive Care Unit Workstation." J *Clinical Monitoring, vol.* 8, No. 1, Jan. 1992: 1-6.

Hall, G. L. & P. B. Colditz, "Continuous Physiological Monitoring: An Integrated System for Use in Neonatal Intensive Care." *Australian Physical & Engineering Sciences in Medicine, vol.* 18, No. 3, 1995; 139-142.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Irazuzta, Jose, "Monitoring in Pediatric Intensive Care." *Indian J. Pediactrics*, vol. 60, 1993: 55-65.

Jans, R. et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Systems" *Critical Care Medicine*, vol. 23, No. 10, Oct. 1995: 1745-1755.

Klass, M. A. & E. Y. Cheng, "Early Response to Pulse Oximetry Alarms with Telemetry." *J. Clinical Monitoring*, vol. 10, No. 3, May 1994: 178-180.

Koski, E. M. J. et al., "A Knowledge-Based Alarm System for Monitoring Cardiac Operated Patients - Assessment of Clinical Performance." *International J Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J. Clinical Monitoring and Computing*, vol. 8, 1992: 289-293.

Laffel, G. et al., "Using Control Charts to Analyze Serial Patient-Related Data." *Quality Management in Health Care*, vol. 3, No.1, Fall 1994: 70-77.

L'Estrange, P. R. et al., "A Microcomputer System for Physiological Data Collection and Analysis." *Australian Dental Journal*, vol. 38, No. 5, Oct. 1993: 400-405.

M. de Beer, N.A. et al., "Clinical Evaluation of a Method for Automatic Detection and Removal of Artifacts in Auditory Evoked Potential Monitoring." *J. Clinical Monitoring*, vol. 11, No. 6, Nov. 1995: 381-391.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Martin, J. F., "Closed-Loop Control of Arterial Pressure During Cardiac Surgery." J. *Clinical Monitoring*, vol. 8, No. 3, Jul. 1992: 252-253.

Meyer, C., "Visions of Tomorrow's ICU." *American J. Nursing*, Apr. 1993: 27-31.

Nenov, V. I. et al., "Computer Applications in the Intensive Care Unit." *Neurosurgery Clinics of North America*, vol. 5, No. 4, Oct. 1994: 811-827.

Nobel, J. J., "Physiological Monitoring Systems, Acute Care." *Pediatric Emergency Care*, vol. 8, No. 4, Aug. 1992: 235-237.

Orr, J. A. & Westenskow, D.R., "A Breathing Circuit Alarm System Based on Neural Networks." *J. Clinical Monitoring*, vol. 10, No. 2, Mar. 1994: 101-109.

Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.

Rampil, I. J., "Intelligent Detection of Artifact." *The Automated Anesthesia Record and Alarm Systems*, Chapter 17, 1987: 175-190.

Runciman, W. B. et al., "The Pulse Oximeter: Applications and Limitations - An Analysis of 2000 Incident Reports." *Anaesthesia and Intensive Care*, vol. 21, No. 5, Oct. 1993: 543-550.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J. Pediatrics*, vol. 60, No. 3, 1993: 469-470.

Schnapp, L. M. & N. J. Cohen, "Pulse Oximetry; Uses and Abuses." *Chest*, vol. 98, No. 5, Nov. 1990: 1244-1250.

Simpson, R. L., "Automating the ICU: Facing the Realities." *Nursing Management*, vol. 23, No. 3, Mar. 1992: 24-26.

Sittig, D. F. & M. Factor, "Physiological Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.

Stoodley, K. D. C. et al., "Problems in the Development of a Computerized Ward Monitoring System for a Pediatric Intensive Care Unit." *International J Clinical Monitoring and Computing*, vol. 8, 1992: 281-287.

Sukavaara, T. et al., "A Knowledge-based Alarm System for Monitoring Cardiac Operated Patients - Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Uckun, S., "Intelligent Systems in Patient Monitoring and Therapy Management." *International J. Clinical Monitoring and Computing*, vol. 11, 1994: 241-253.

Webb, R. K., "Medical Decision Making and Decision Analysis." *Anesthesia and Intensive Care*, vol. 16, No. 1, Feb. 1988: 107-109.

Yien, H. et al., "Spectral Analysis of Systemic Arterial Pressure and Heart Rate Signals as a Prognostic Tool for the Prediction of Patient Outcome in the Intensive Care Unit" *Critical Care Medicine*, vol. 25, No. 4, 1997: 614-619.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L.. "Reducing False Alarms in the Intensive Care Unit: A Systematic Comparison of Four Algorithms" Proceedings *AMIA* Symposium, 1997. pp. 9-14 (unnumbered).

Tsien, Christine L. "Reducing False Alarms in the Intensive Care Unit: A Systematic Comparison of Four Algorithms" Proceedings Annual *AMIA* Fall Symposium (1997), p. 894.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

* cited by examiner

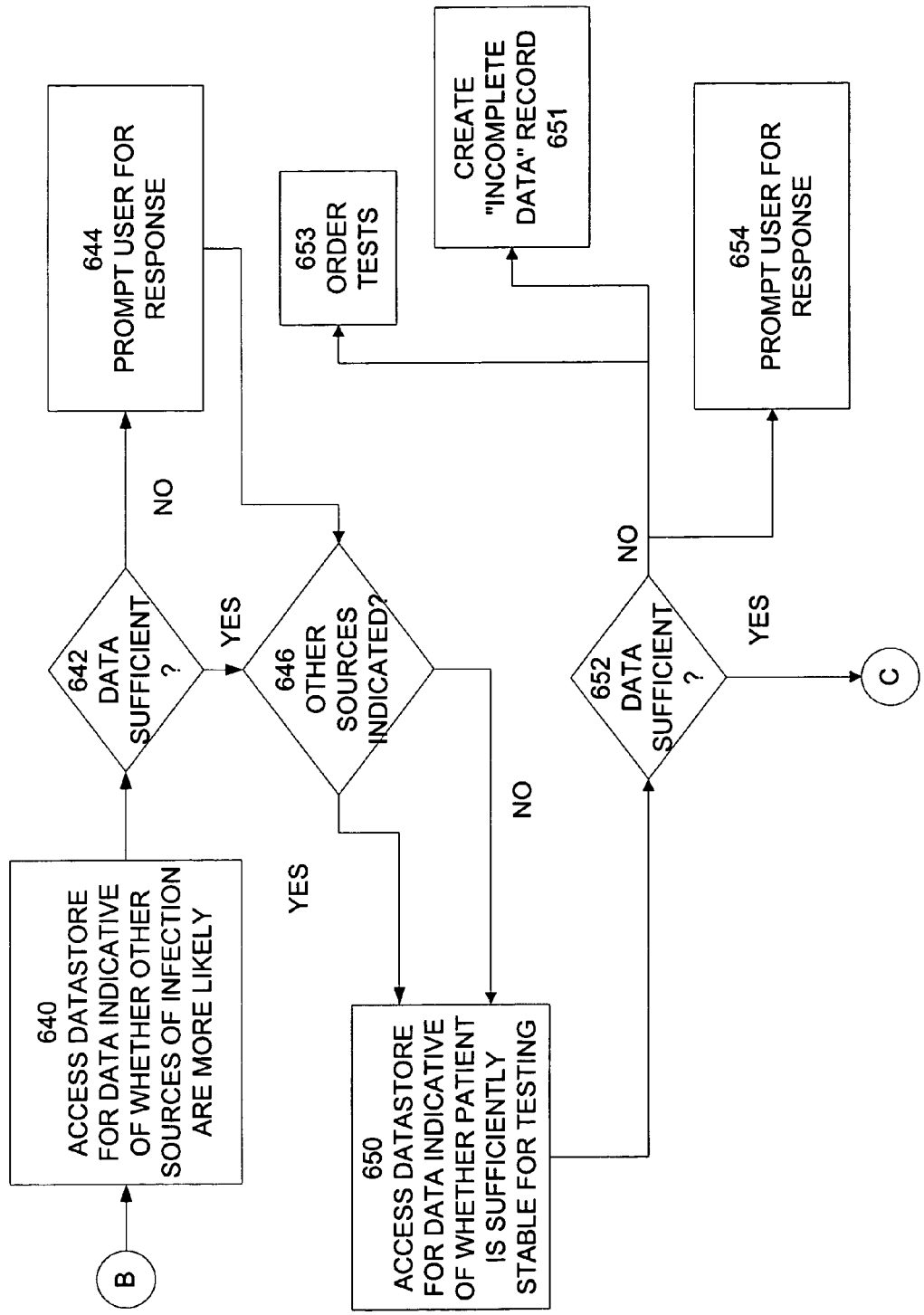

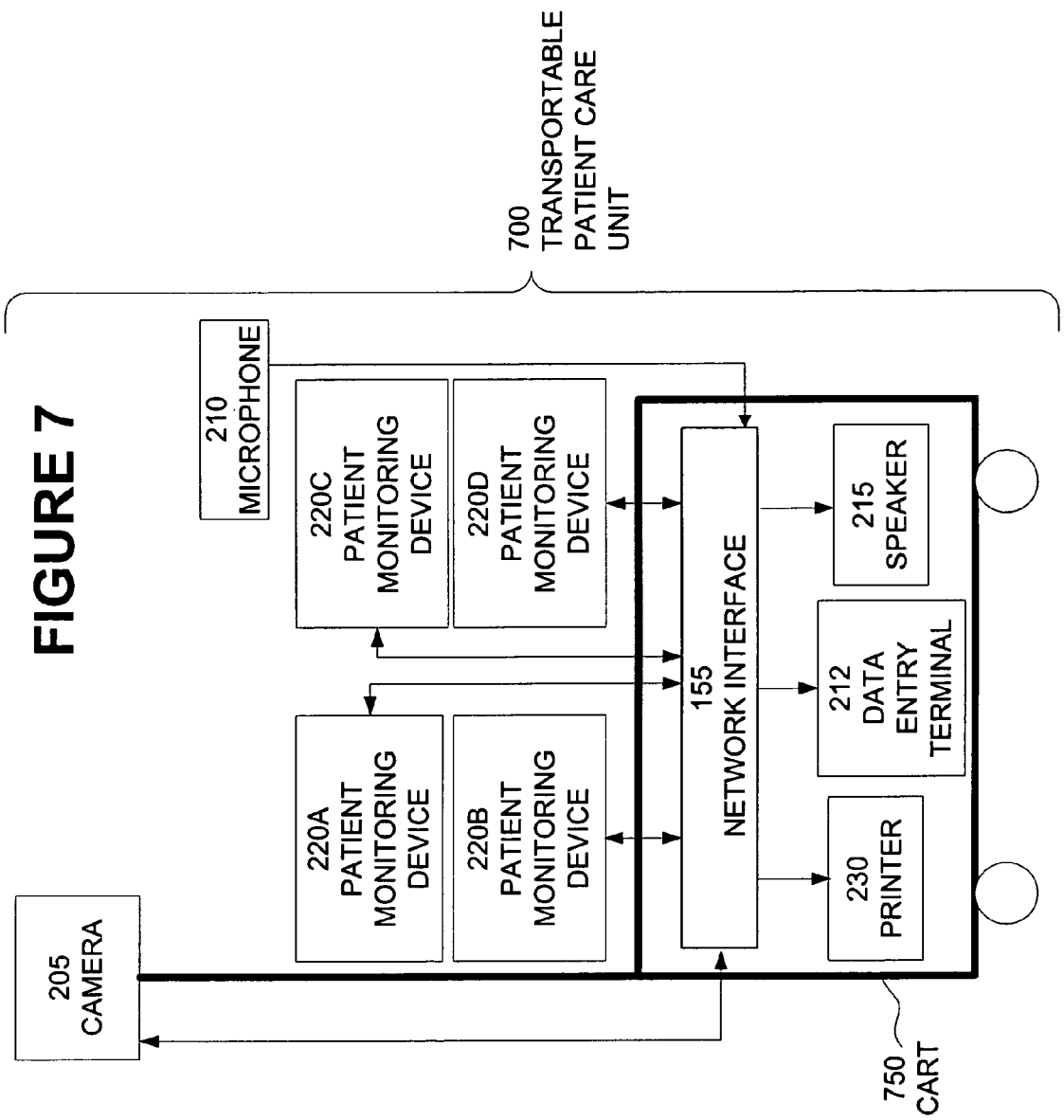

TELECOMMUNICATIONS NETWORK FOR REMOTE PATIENT MONITORING

CROSS REFERENCE TO RELATED APPLICATIONS

This application claims priority under 35 U.S.C. § 120 as a continuation-in-part of U.S. application Ser. No. 09/443,072 filed Nov. 18, 1999, now U.S. Pat. No. 6,804,656 issued Oct. 12, 2004, which claims the benefit of U.S. Provisional Application No. 60/141,520, filed Jun. 23, 1999.

BACKGROUND

This invention relates generally to a communication system for medical applications and monitoring of equipment used in the care of hospitalized patients. More particularly this invention uses a telecommunications network to provide a real-time, continuous data transfer from patient monitoring equipment into a computer system that continuously assesses such monitored data for medical assessment, tracking of progress of treatment, and other applications for hospitalized patients in geographically dispersed locations.

While the severity of illness of hospitalized patients over the past 15 years has increased dramatically, the level of and type of care of those patients has remained constant. Most hospitalized patients receive brief minutes of attention during morning rounds from physicians with limited critical care experience. During the remainder of the day and night, nurses are the primary caregivers, with specialists called only after patient conditions have started to deteriorate. The result of this mismatch between severity of illness and physician coverage is an unacceptably high mortality rate. In ICUs, where patients are assumed to get the best care, the mortality rate is 10% nationwide, and marked by a high prevalence of avoidable errors that result in clinical complications. In 1998, the Institute of Medicine (IOM) determined that avoidable patient complications were responsible for 98,000 deaths per year and was the single largest problem in medical care delivery. A 2003 study estimated that 18 patient safety indicators attributed $9.3 billion in excess charges per year and a more recent study (Health Grades Quality Study—July 2004) estimated that the IOM study had grossly underestimated the avoidable deaths and that the figure was closer to 190,000 deaths per year.

Numerous studies have shown that increasing the involvement of skilled care providers with patients can markedly improve patient outcomes. While providing additional skilled care providers would seem an obvious solution, current trends suggest that the demand for skilled care providers will continue to exceed the supply.

Attempts to automate various aspects of patient care have been the subject of various inventions. For example, U.S. Pat. No. 5,868,669 to Iliff was issued for "Computerized Medical Diagnostic and Treatment Advice System." The disclosed invention is for a system and method for providing computerized knowledge based medical diagnostic and treatment advice to the general public over a telephone network.

U.S. Pat. No. 5,823,948 to Ross, Jr. et al was issued for "Medical Records Documentation, Tracking and Order Entry System". The disclosed invention is for a system and method that computerizes medical records, documentation, tracking and order entries. A teleconferencing system is employed to allow patient and medical personnel to communicate with each other. A video system can be employed to videotape a patient's consent.

U.S. Pat. No. 4,878,175 to Norden-Paul et al. was issued for A Method for Generating Patient-Specific Flowsheets By Adding/Deleting Parameters." The disclosed invention is for an automated clinical records system for automated entry of bedside equipment results, such as an EKG monitor, respirator, etc. The system allows for information to be entered at the bedside using a terminal having input means and a video display.

U.S. Pat. No. 5,544,649 to David et al. was issued for Ambulatory Patient Health Monitoring Techniques Utilizing Interactive Visual Communications." The disclosed invention is for an interactive visual system, which allows monitoring of patients at remote sites, such as the patient's home. Electronic equipment and sensors are used at the remote site to obtain data from the patient, which is sent to the monitoring site. The monitoring site can display and save the video, audio and patients data.

U.S. Pat. No. 5,867,821 to Ballantyne et al. was issued for "Method and Apparatus for Electronically Accessing and Distributing Personal Health Care Information and Services in Hospitals and Homes." The disclosed invention is for an automated system and method for distribution and administration of medical services, entertainment services, and electronic health records for health care facilities.

U.S. Patent No. 5,832,450 to Myers et al. issued for "Electronic Medical Record Using Text Database." The disclosed invention is for an electronic medical record system, which stores data about patient encounters arising from a content generator in freeform text.

U.S. Pat. No. 5,812,983 to Kumagai was issued for "Computer Medical File and Chart System." The disclosed invention is for a system and method which integrates and displays medical data in which a computer program links a flow sheet of a medical record to medical charts.

U.S. Pat. No. 4,489,387 to Lamb et al. was issued for "Method and Apparatus for Coordinating Medical Procedures." The disclosed invention is for a method and apparatus that coordinates two or more medical teams to evaluate and treat a patient at the same time without repeating the same steps.

U.S. Pat. No. 4,731,725 to Suto et al. issued for "Data Processing System which Suggests a Pattern of Medical Tests to Reduce the Number of Tests Necessary to Confirm or Deny a Diagnosis." The disclosed invention is for a data processing system that uses decision trees for diagnosing a patient's symptoms to confirm or deny the patient's ailment.

U.S. Pat. No. 5,255,187 to Sorensen issued for "Computer Aided Medical Diagnostic Method and Apparatus." The disclosed invention is for an interactive computerized diagnostic system which relies on color codes which signify the presence or absence of the possibility of a disease based on the symptoms a physician provides the system.

U.S. Pat. No. 5,839,438 to Chen et al. issued for "Intelligent Remote Visual Monitoring System for Home Health Care Service." The disclosed invention is for a computer-based remote visual monitoring system, which provides in-home patient health care from a remote location via ordinary telephone lines.

U.S. Pat. No. 5,842,978 to Levy was issued for "Supplemental Audio Visual Emergency Reviewing Apparatus and Method." The disclosed invention is for a system which videotapes a patient and superimposes the patient's vital statistics onto the videotape.

U.S. Pat. No. 6,364,834 issued to Reuss, et al. was issued for a "Method and System for Remotely Monitoring Multiple Medical Parameters in an Integrated Medical Monitoring System." The disclosed invention is for an integrated medical monitoring system having a patient monitor, a central monitor, and a remote access device. Each of these devices is tied together through an integrated communications link. The communications between various components of the system are bi-directional, an attribute described as affording the opportunity to change data sampling rates and select which parameters to monitor from the remote location The thrust of the Reuss Patent is the collection of data from monitors so that the data are available to a caregiver. The caregiver may view the data on a display or request the data for viewing.

U.S. Pat. No. 4,838,275 issued to Lee for a "Home Medical Surveillance System," describes an apparatus for use in a patient's home that includes special furniture on which the patient lies and sits. Embedded in this special furniture are devices that automatically sense multiple parameters related to the patient's health. The disclosed invention is directed to monitoring individual ambulatory patients in a home environment. However, this monitoring is not stated to be continuous.

U.S. Pat. No. 3,646,606 issued to Buxton et al. for a "Physiological Monitoring System," describes an apparatus for measuring physiological parameters indicative of the condition of a patient and sending those parameters to a central monitoring station. The central monitoring station would display the parameters in analog and digital form issue an alert signal in the event certain parameter values are detected. Viewing patient data is accomplished by selecting a patient using a switch (FIG. 3, callout 122). Thus, not all patients are monitored at all times. The described invention is directed to a data gathering system combined with a single event driven process to manage "emergencies." Data is presented to a single operator and, except for certain alert conditions, the evaluation of that data is charged to the single operator.

While these inventions provide useful records management and diagnostic tools, none of them provides a comprehensive communications system that incorporates for monitoring and providing real time continuous assessment and intervention of monitored hospitalized patients at disparate patient monitoring stations.

What would be useful would be a communication network for automated monitoring of multiple hospitalized patients, capable of using diverse data sources to provide a continuous assessment of a patient's condition. Such a network would support computerized diagnostic tools to aid caregivers in identifying and treating hospitalized patients who would benefit from monitoring and assessment. Such a network would further comprise the ability to flexibly and individually establish and/or revise alerts for patients from a central location based on individualized patient parameters and to utilize computer based algorithms to a communications network optimized for intervening appropriately.

SUMMARY

An embodiment of the present invention uses a telecommunications network to facilitate real-time, continuous assessment of hospitalized patients in geographically dispersed locations. For the purpose of this and other embodiments of the present invention, a "hospitalized patient" refers to a person admitted to a treatment facility capable of providing twenty-four hour care. By way of illustration and not as a limitation, a treatment facility may be a hospital, a nursing home, or other long-term institution that is capable of providing twenty-four hour care. A patient may be selected for monitoring based on criteria established by the treatment facility. By way of illustration and not as a limitation, a 'monitored patient" comprises a critically ill patient, an acutely ill patient, a patient with a specific illness, an emergency room patient, an operating room patient, and a patient with an uncertain diagnosis.

Patient monitoring equipment acquires monitored data elements from a hospitalized patient which can come from a patient monitoring station and transmits the monitoring data over a network to a remote command center. Monitored data comprises physiological data elements, video data elements, and audio data elements. The remote command center receives the monitoring data from all of the patient monitoring stations. The remote command center also accesses other data relating to the condition of a patient. By way of illustration and not as limitation, the remote command center has access to data relating to personal information about the patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data"). The data available to the remote command center over the network, that is, the monitoring data and the patient data, is collectively referred to as "assessment data."

A rules engine continuously applies a patient-specific rule or rule set to the data elements selected from the assessment data from each monitored hospitalized patient to determine whether the patient-specific rule for that site has been contravened. In the event the patient-specific rule has been contravened, an alert at the remote command center is triggered. Patient-specific rules for each monitored hospitalized patient may be established and changed at the remote command center for each as the patients' conditions warrant. In one embodiment of the present invention, a patient-specific rule is established to determine whether a patient's condition is deteriorating. In another embodiment, a patient specific rule is established to determine whether a patient's condition is improving. In yet another embodiment of the present invention, an alert that a patient-specific rule has been contravened comprises advice on treatment of the patient.

Another embodiment of the present invention provides continued care software that uses elements of the assessment data to provide decision support and that prompts a user for input to provide decision support to caregivers. A decision support algorithm responds to elements of assessment data to produce textural material describing a medical condition, scientific treatments and possible complications. This information is available in real time to assist in all types of clinical decisions from diagnosis to treatment to triage.

In still another embodiment of the present invention, order writing software facilitates the ordering of procedures and medications using patient-specific data. The order writing software and the continued care software are interactive allowing a caregiver to access features of both applications simultaneously, so that patient orders are given that are consistent and not conflicting with a patient's status and condition (i.e., allergies to medications or medications that may conflict with the order in question).

In yet another embodiment of the present invention, a video visitation system allows remote visitation participants (RVPs) at remote terminals to participate in a video/audio conferencing session with a local visitation participant (LVP) (e.g., the patient or the patient's caregivers) at a patient site.

It is therefore an aspect of the present invention to receive at a remote command center monitoring data from a monitored hospitalized patient over a communications network.

It is another aspect of the present invention to make available other data relating to the condition of a patient to the remote command center.

It is yet another aspect of the present invention to establish and/or revise patient specific rules at the remote command center and to apply a rules engine to "assessment data" to determine whether a patient-specific rule is contravened.

It is another aspect of the present invention to determine based on assessment data whether the condition of a monitored hospitalized patient warrants revising a patient-specific rule at the remote command center.

It is still another aspect of the present invention to issue an alert from the remote command center in the event a patient-specific rule is contravened.

It is an aspect of the present invention to provide treatment information in an order for an intervention issued by the remote command center to a treatment facility where a monitored hospitalized patient is receiving care.

It is a further aspect of the present invention to apply decision support algorithms to data relating to the condition of a patient to provide decision support to caregivers.

It is another aspect of the present invention to provide a video visitation system that allows a remote visitation participant to participate in a video/audio conferencing session with a patient and/or a local visitation participant.

In an embodiment of the present invention, a hospitalized patient care system comprises a telecommunication network and monitoring stations. The monitoring stations comprise monitoring equipment adapted to monitor data elements from geographically dispersed hospitalized patients and to send the monitored data elements to a remote command center via the telecommunications network. In an embodiment of the present invention, monitoring equipment comprises physiological sensors and monitored data elements comprise physiological data elements. In still another embodiment of the present invention, monitoring equipment comprises a video imaging system that sends video image data elements to the remote command center and a voice communication system that sends audio data elements to remote command center.

The remote command center receives the monitored data elements from the geographically dispersed hospitalized patients, accesses patient data elements indicative of a medical condition associated with each of the geographically dispersed hospitalized patients, establishes patient-specific rules associated with each of the geographically dispersed hospitalized patients, and applies the patient-specific rules continuously and simultaneously using a rules engine. In an embodiment of the present invention, a patient specific rule comprises an algorithm.

The rules engine selects data elements from the monitored data elements and the patient data elements associated with a hospitalized patient, applies a patient-specific rule associated with the hospitalized patient to the selected data elements, determines whether the patient-specific rule for the hospitalized patient has been contravened; and in the event the patient-specific rule for the hospitalized patient has been contravened, issues an alert from the remote command center. By way of illustration and not as a limitation, the alert comprises a patient intervention protocol and order.

In an embodiment of the present invention, the selected data elements comprise a physiological data element of the hospitalized patient and a clinical data element of the hospitalized patient. In an alternate embodiment of the present invention, the selected data elements comprise a physiological data element of the hospitalized patient and a medication data element of the hospitalized patient. In yet another embodiment of the present invention, the selected data elements comprise a physiological data element of the hospitalized patient and a laboratory data element of the hospitalized patient. In still another embodiment of the present invention, the selected data elements comprise a clinical data element of the hospitalized patient and a laboratory data element of the hospitalized patient. In another embodiment of the present invention, the selected data elements comprise a physiological data element of the hospitalized patient and another physiological data element of the hospitalized patient. In yet another embodiment of the present invention, the selected data elements comprise at least two data elements of the hospitalized patient selected from the group consisting of a physiological data element, a clinical data element of the hospitalized patient, a medication data element of the hospitalized patient, and a laboratory data element of the hospitalized patient.

Additionally, the rules engine determines whether the hospitalized patient requires monitoring by the monitoring station. In the event the hospitalized patient does not require monitoring by the monitoring station, the rules engine issues a release protocol and order.

In another embodiment of the present invention, the hospitalized patient care system further comprises an audio/video teleconferencing server. The audio/video teleconferencing server bridges a local visitation terminal and a remote visitation terminal, sends audio and video signals generated by the local visitation terminal to the remote visitation terminal, sends audio and video signals generated by the remote visitation terminal to the local visitation terminal, and provides the audio data elements and video image data elements to both the remote visitation terminal and the local visitation terminal.

Additionally, the hospitalized patient care system accesses a decision support algorithm and applies the decision support algorithm to selected data elements of a hospitalized patient and user input to provide patient care advice to the user. Patient care advice may be a diagnosis, a method of treatment, and a laboratory procedure. As will be appreciated by those skilled the art, patient care advice may take other forms without departing from the scope of the present invention.

The patient support system may also access an order writing module that issues orders. By way of illustration and not as a limitation, the order writing module may authorize administering medication to a hospitalized patient, authorize subjecting the hospitalized patient to a laboratory protocol, and subjecting the hospitalized patient to a surgical procedure.

An embodiment of the present invention provides a method for continuous assessment of geographically dispersed hospitalized patients. Monitored data elements from geographically dispersed hospitalized patients are received at a remote command center. By way of illustration and not as a limitation, monitored data elements comprise physiological data elements, video image data elements and audio data elements.

In an embodiment of the present invention, patient data elements indicative of a medical condition associated with each of the geographically dispersed hospitalized patients are accessed. Patient-specific rules associated with each of the geographically dispersed hospitalized patients are established. Data elements from the monitored data elements associated with the hospitalized patient and the patient data elements associated with a hospitalized patient are selected and a patient-specific rule associated with the hospitalized patient is applied to the selected data elements.

A determination is made whether the patient-specific rule for the hospitalized patient has been contravened. In the event the patient-specific rule for the hospitalized patient has been contravened, an alert is issued from the remote command center. By way of illustration and not as a limitation, an alert comprises a patient intervention protocol and order. Additionally, a determination is made whether the hospitalized patient requires monitoring by the monitoring station. In the event the hospitalized patient does not require monitoring by the monitoring station, the rules engine issues a release protocol and order.

In an embodiment of the present invention, the selected data elements comprise a physiological data element of the hospitalized patient and a clinical data element of the hospitalized patient. In an alternate embodiment of the present invention, the selected data elements comprise a physiological data element of the hospitalized patient and a medication data element of the hospitalized patient. In yet another embodiment of the present invention, the selected data elements comprise a physiological data element of the hospitalized patient and a laboratory data element of the hospitalized patient. In still another embodiment of the present invention, the selected data elements comprise a clinical data element of the hospitalized patient and a laboratory data element of the hospitalized patient. In another embodiment of the present invention, the selected data elements comprise a physiological data element of the hospitalized patient and another physiological data element of the hospitalized patient. In yet another embodiment of the present invention, the selected data elements comprise at least two data elements of the hospitalized patient selected from the group consisting of a physiological data element, a clinical data element of the hospitalized patient, a medication data element of the hospitalized patient, and a laboratory data element of the hospitalized patient.

In an embodiment of the present invention, a local visitation terminal and a remote visitation terminal are bridged. Audio and video signals generated by the local visitation terminal are sent to the remote visitation terminal and audio and video signals generated by the remote visitation terminal are sent to the local visitation terminal. The audio data elements and video image data elements are provided to both the remote visitation terminal and the local visitation terminal.

Another embodiment of the present invention provides a method wherein a decision support algorithm is accessed. The decision support algorithm is applied to selected data elements of a hospitalized patient and to user input to provide patient care advice to the user. Patient care advice may be in the form of a diagnosis, a method of treatment, and a laboratory procedure. As will be appreciated by those skilled the art, patient care advice may take other forms without departing from the scope of the present invention.

The patient support system may also access an order writing module that issues orders. By way of illustration and not as a limitation, the order writing module may authorize administering medication to a hospitalized patient, authorize subjecting the hospitalized patient to a laboratory protocol, and subjecting the hospitalized patient to a surgical procedure.

DESCRIPTION OF THE FIGURES

FIG. 7 illustrates the components of a transportable patient care unit according to embodiments of the present invention.

DETAILED DESCRIPTION

Figure 1:
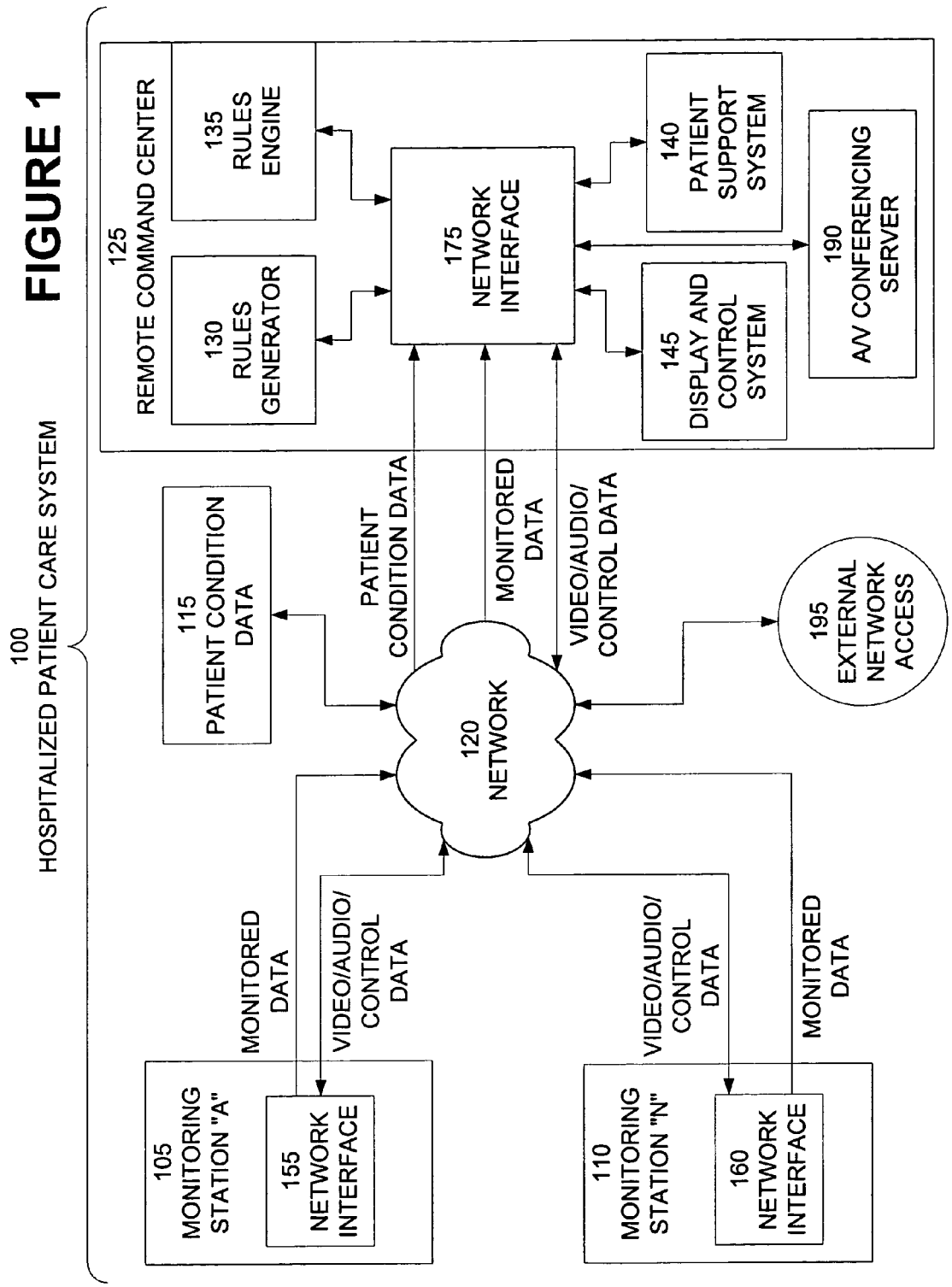
FIG. 1 illustrates a block diagram of the components of a hospitalized patient care system (HPCS) according to embodiments of the present invention.

The following terms used in the description that follows. The definitions are provided for clarity of understanding:

assessment data—assessment data is all data relevant to the health of a patient.

caregiver—an individual providing care to a patient. Examples include a nurse, a doctor, medical specialist (for example and without limitation an intensivist, cardiologist or other similar medical specialist).

clinical data—data relating to the observed symptoms of a medical condition.

hospitalized patient—a person admitted to a treatment facility capable of providing twenty-four hour care.

monitored data—data received from monitoring devices connected to a monitored hospitalized patient.

monitored hospitalized patient—a hospitalized patient from whom monitored data is collected and whose condition is subject to continuous real-time assessment from a remote command center.

patient data—data relating to a patient's diagnosis, prescriptions, history, condition, laboratory results and other health-relevant data.

physiological data—any data relating to the functions of the human body and its processes.

symptom—any sign or indication of a health condition that can be identified from patient reports and/or assessment data.

An embodiment of the present invention uses a telecommunications network to facilitate real-time, continuous assessment of hospitalized patients in geographically dispersed locations. Patient monitoring equipment acquires monitoring data from a hospitalized patient associated with a patient monitoring station and transmits the monitoring data over a network to a remote command center. The remote command center receives the monitoring data from all of the patient monitoring stations. The remote command center also accesses other data relating to the condition of a patient such as the "patient data" as defined above. The data available to the remote command center over the network, that is, the monitoring data and the patient data, is collectively referred to as "assessment data."

A rules engine continuously applies a patient-specific rule (or series of rules) to the selected data elements of the assessment data from each monitored hospitalized patients to determine whether the patient-specific rule for a hospitalized patient has been contravened. In the event the patient-specific rule has been contravened, an alert at the remote command center is issued. Patient-specific rules for each monitored hospitalized patient may be established and changed at the remote command center for each as the patients' conditions warrant. In one embodiment of the present invention, a patient-specific rule is established to determine whether a patient's condition is deteriorating. In another embodiment, a patient specific rule is established to determine whether a patient's condition is improving. In yet another embodiment of the present invention, an alert that a patient-specific rule has been contravened comprises advice on treatment of the patient.

Another embodiment of the present invention applies continued care software to selected data elements of the assessment data and user input to provide decision support to caregivers. A decision support algorithm responds to data relating to the condition of a patient to produce prompts for additional input or textural material describing a medical condition, scientific treatments and possible complications. This information is available in real time to assist in all types of clinical decisions from diagnosis to treatment to triage.

FIG. 1 illustrates a block diagram of the components of a hospitalized patient care system (HPCS) according to embodiments of the present invention. A HPCS 100 comprises a plurality of patient monitoring stations. Patient monitoring station "A" 105 and patient monitoring station "N" 110 are illustrated, but the invention is not so limited. For the sake of clarity, the description that follows will refer to patient monitoring station "A" 105. However, the description applies to all patient monitoring stations within the HPCS 100.

Patient monitoring station "A" 105 is connected to network 120 via network interface 155. Network 120 is preferably a broadband network and may be wired, optical, wireless or a combination of wired, optical or wireless. Also connected to network 120 is remote command center 125. Remote command center 125 comprises a patient rules generator 130, a rules engine 135, patient support system 140, display and control system 145, and audio/video (A/V) conferencing server 190. A network interface 175 provides connectivity between network 120 and the other elements of the remote command center. Network 120 is configured to permit access to external networks 195, such as the Internet.

Figure 2:
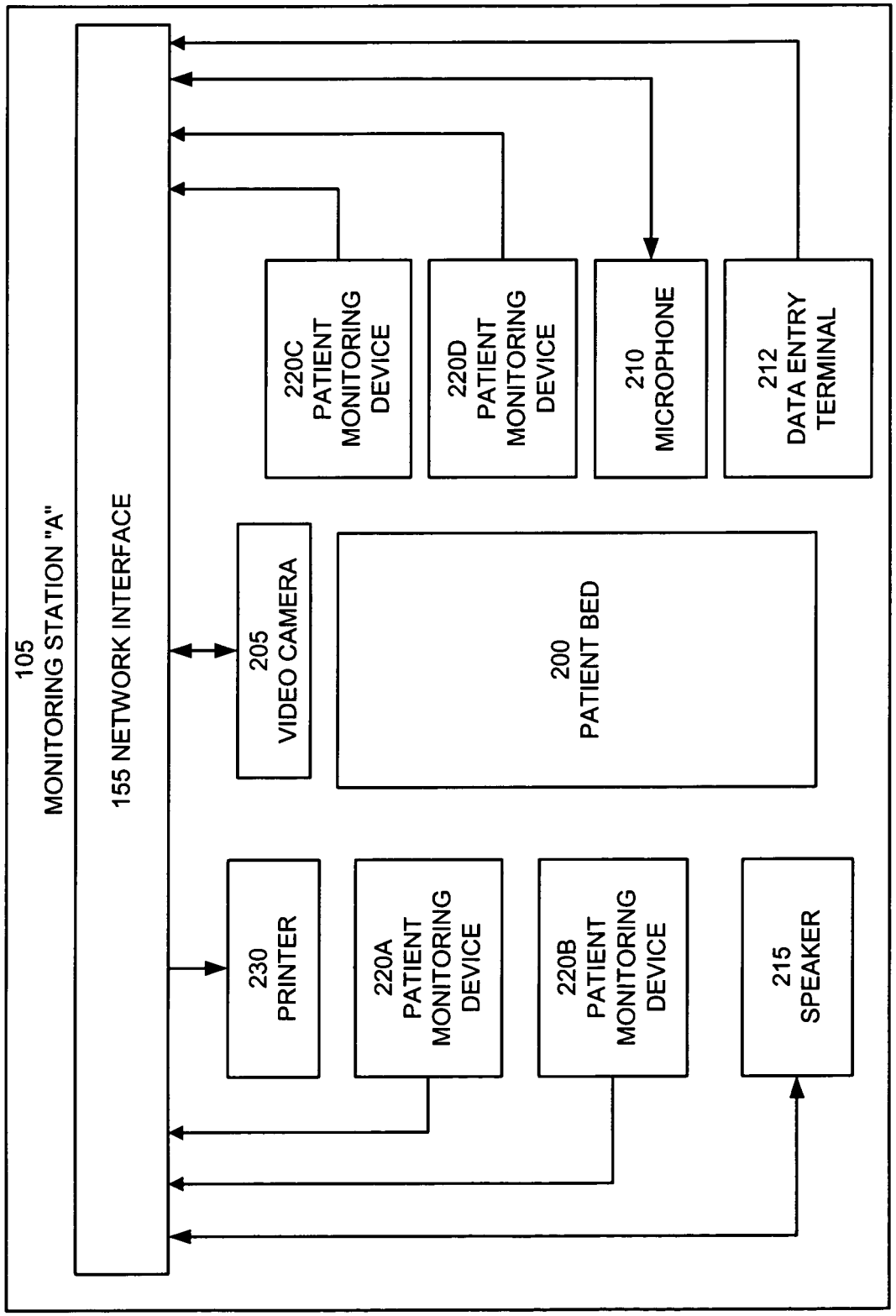
FIG. 2 illustrates a block diagram of a patient monitoring station according to an embodiment of the present invention.

FIG. 2 illustrates a block diagram of a patient monitoring station according to an embodiment of the present invention. Referring to FIG. 1 and FIG. 2, patient monitoring station "A" 105 comprises a patient bed 200. A data entry means such as a keyboard, touchpad or similar data entry means known in the art 212 allows on site care givers to provide additional data that may be germane to the care of the patient. Video camera 205 is movable both horizontally and vertically and zoomable through remote commands from the display and control system 145 of remote command center 125 so that specific views of the patient may be obtained both up close and generally. A microphone 210 and a speaker 215 permit both one-way audio monitoring of the patient and two-way communication with the patient or others located in patient monitoring station "A" 105. Patient monitoring devices 220A-220D acquire physiological data from a patient in real-time. A printer 230 receives and prints orders from an authorized remote caregiver. By way of illustration and not as a limitation, an order comprises a lab order, a medication, and a procedure. A network interface 155 provides access to network 120 for transmission of the monitored data, video signal, and audio signals to the remote command center 125 and the receipt of the audio signals and printer signals at the monitoring station.

Patient monitoring station "A" 105 may be implemented in an intensive care unit, an operating room, a post-operation recovery unit, an emergency room, or any site where a hospitalized patient receives care in accordance with the embodiments of the present invention. Patient monitoring station "A" 105 may be a dedicated site or may be a site that has been equipped to perform the functions of a patient monitoring station on a temporary basis. By way of illustration and not as a limitation, FIG. 7 illustrates the components of a transportable patient care unit according to embodiments of the present invention. A transportable patient care unit 700 comprises the components illustrated in FIG. 2 mounted on a cart 750. Video camera 205 is movable both horizontally and vertically and zoomable through remote commands from the display and control system 145 of remote command center 125 so that specific views of the patient may be obtained both up close and generally. A microphone 210 and a speaker 215 permit both one-way audio monitoring of the patient and two-way communication with the patient or others located in proximity to patient monitoring station "A" 105. Patient monitoring devices 220A-220D acquire physiological data from a patient in real-time. A printer 230 receives and print orders from an authorized caregiver. By way of illustration and not as a limitation, an order comprises a lab order, a medication, and a procedure. A network interface 155 provides access to network 120 for transmission of the monitored data, video signal, and audio signals to the remote command center 125 and the receipt of the audio signals and printer signals at the monitoring station. A data entry means such as a keyboard, touchpad or similar data entry means known in the art 212 allows on site care givers to provide additional data that may be germane to the care of the patient.

The remote command center 125 receives monitored data from patient monitoring station "A" 105 and patient condition data 115 via network 125 through network interface 175. Monitored data comprises real-time data received from monitoring equipment at patient monitoring station "A" 125 that is configured to receive physiological data from a patient requiring critical care and associated with patient monitoring station "A." The remote command center also receives "patient condition data" 115 applicable to the patient associated with patient monitoring station "A" 105. Patient condition data comprises data relating to a patient's diagnosis, prescriptions, history, condition, laboratory results and other health-relevant data.

The rules generator 130 and the rules engine 135 facilitate detection of impending problems and automate problem detection thereby allowing for intervention before a patient condition reaches a crisis state. The rules engine 135 continuously applies a patient-specific rule to selected data elements of the assessment data 115 to determine whether the patient-specific rule for a hospitalized patient has been contravened. In the event the patient-specific rule has been contravened, the remote command center issues an alert. In one embodiment of the present invention, a patient-specific rule is established to determine whether a patient's condition is deteriorating and an alert comprises an intervention order and protocol. In another embodiment of the present invention, the rules engine is further adapted to determine whether a monitored hospitalized patient requires monitoring by a monitoring station. If not, a release protocol and order are issued.

Patient-specific rules may be established and revised at the remote command center for the hospitalized patient associated with each patient monitoring station. Thus, rules engine generator 130 establishes one or more rules for the hospitalized patient associated with patient monitoring station "A" 105. By way of illustration, a patient-specific rule dictates threshold limits for changes over time of specific vital sign data. Thresholds that are patient-specific disease-specific are established. The rules engine then evaluates the monitored data for the specific vital sign data to determine if a change threshold has been exceeded.

For example, a patient with coronary artery disease can develop myocardial ischemia with relatively minor increases in heart rate. Heart rate thresholds for patients with active ischemia (e.g. those with unstable angina in a coronary care unit) are set to detect an absolute heart rate of 75 beats per minute. In contrast, patients with a history of coronary artery disease in a surgical ICU have thresholds set to detect either an absolute heart rate of 95 beats per minute or a 20% increase in heart rate over the baseline. For this threshold, current heart rate, calculated each minute based on the median value over the preceding 5 minutes, is compared each minute to the baseline value (the median value over the preceding 4 hours).

In another embodiment of the present invention, a patient-specific rule is based on multiple variables. By way of illustration, a patient-specific rule is contravened if the rules engine determines that monitored data reflects both a simultaneous increase in heart rate of 25% and a decrease in blood pressure of 20%, occurring over a time interval of 2 hours.

For multi-variable patient-specific rules, thresholds rely on known or learned associations between changes in multiple variables, which variables may comprise diverse data types. Thus, a patient-specific rule may associate monitored physiological data with patient clinical data. The association may change depending on the diagnosis of the patient, the medication given the patient, and the results of laboratory data. For example, a patient-specific rule may associate central venous pressure and urine output, because simultaneous decreases in these two variables can indicate that a patient is developing hypovolemia. Another patient-specific rule may cause the rules engine to evaluate laboratory data (e.g. looking for need to exclude active bleeding and possibly to administer blood).

In an embodiment of the present invention, a patient-specific rule established for a hospitalized patient and the hospitalized patient is associated with a particular monitoring station. In this embodiment, if the patient were associated with a different monitoring station, the remote command center would associate the patient-specific rule with the different monitoring station at the time that the association between the hospitalized patient and the different monitoring station is made. In this way, patient specific rules "move" with the patient without manual intervention.

Figure 3:
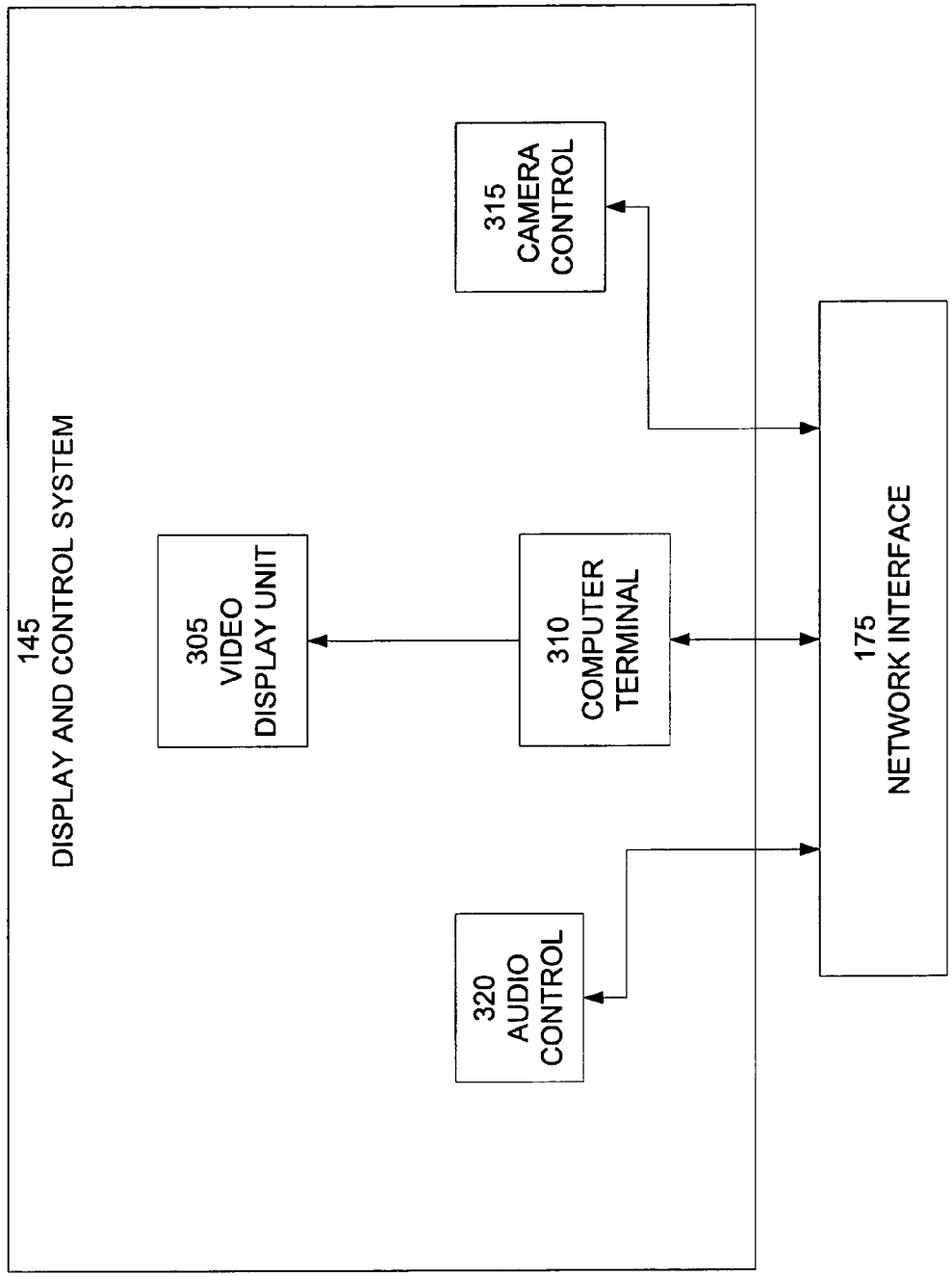
FIG. 3 illustrates a display and control system according to an embodiment of the present invention.

Referring to FIG. 1, the display and control system 145 provides the human interface for the remote command center. FIG. 3 illustrates a display and control system according to an embodiment of the present invention. A display and control system 145 comprises a video display unit 305, a computer terminal 310, a camera control 315, and an audio control 320. The video display unit 305 displays real-time monitoring data and video images from patient monitoring station "A" 105. The computer terminal 310 allows selecting the layout and content displayed on the video display unit 305, provides access to the record of the patient associated with patient monitoring station "A" 105, and permits entry of data into that record. The camera control 315 permits control from the remote command center 125 of the video camera 205 (see FIG. 2) at the patient monitoring station "A" 105. The audio control permits control from the remote command center 125 of a microphone 210 and a speaker 215 within patient monitoring station "A" 105. Connectivity between the components of the display and control systems 145 and patient monitoring station "A" 105 is provided by network interface 175, network 120, and network interface 155.

Figure 4:
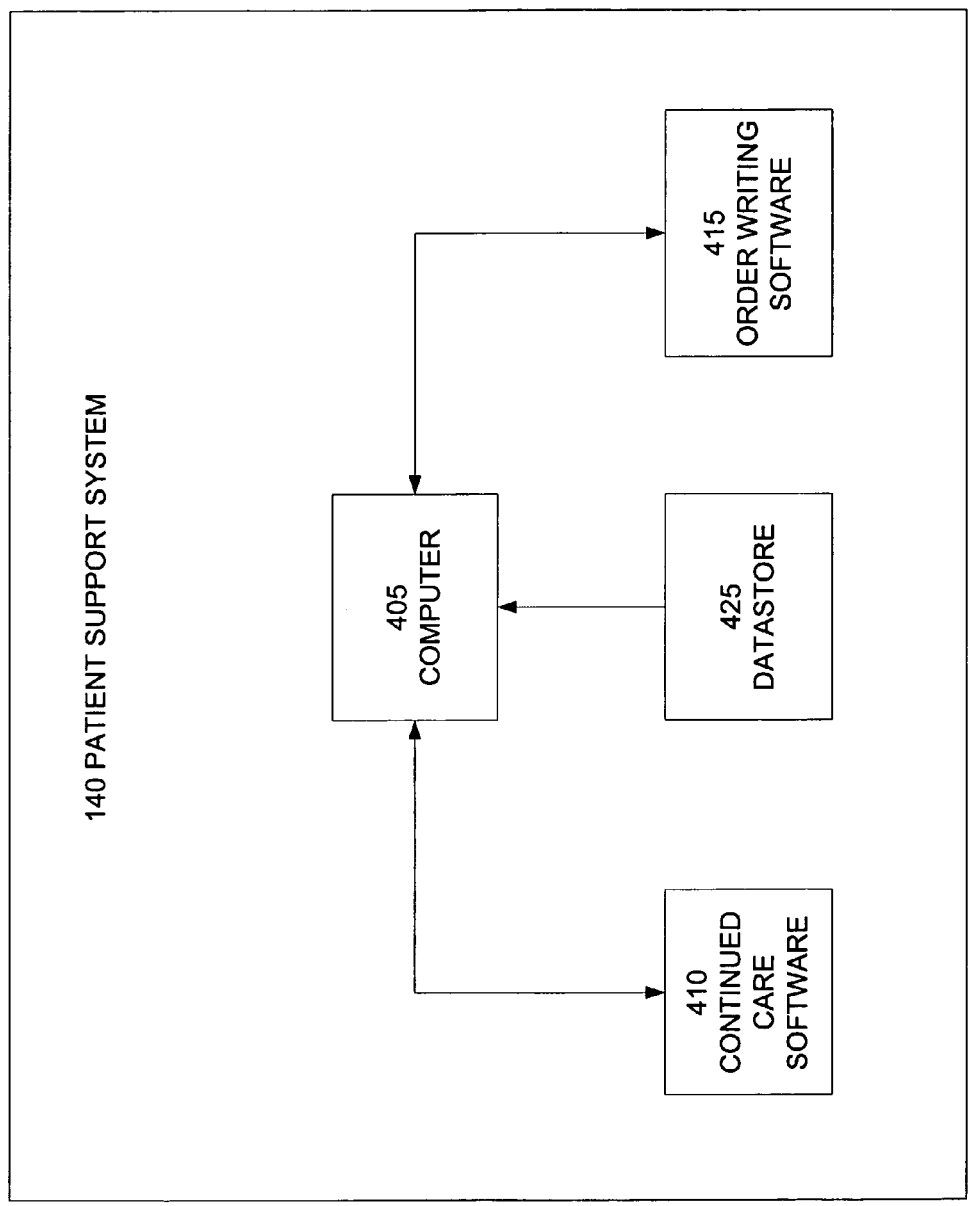
FIG. 4 illustrates a patient support system according to an embodiment of the present invention.

Referring again to FIG. 1, the remote command center 125 comprises patient support system 140. FIG. 4 illustrates a patient support system according to an embodiment of the present invention. Referring to FIG. 4, patient support system 140 comprises a computer 405. Computer 405 operates continued care software 420 and order writing software 415. Diagnostic software 410 and order writing software 415 make calls to datastore 425 to access the assessment data related to a particular hospitalized patient associated with patient monitoring station "A" 105 (see, FIG. 1).

Continued care software 420 comprises decision support algorithms that operate on elements of assessment data and/or input from a caregiver to facilitate decisions relating to diagnosis, treatment and triage. Continued care software may be applied at the time the patient is admitted and throughout the patient's stay within a treatment facility. Thus, a diagnosis may be made based on the initial data acquired during admission, following the completion of laboratory procedures, or after other pertinent information is acquired. In an embodiment of the present invention, continued care software 420 evaluates continuously, selected data elements of assessment data and provides an alert if those data are indicative of a different diagnosis. The alert may take the form of suggested diagnoses that are vetted by a series of questions posed by the continued care software 420 to a caregiver. Based on the responses to the questions, a suggested diagnosis may be eliminated. The alert may also comprise instructions for specific tests to be run on the monitored hospitalized patient to help formulate a new diagnosis. Once a diagnosis is confirmed, the continued care software 420 continues to monitor changes in patient data and issues an alert if the current diagnosis should be reevaluated by a caregiver.

In still another embodiment of the present invention, continued care software 420 operates on a diagnosis to "triage" a patient. For example and without limitation a caregiver requests an Apache II score based on the diagnosis. Continued care software 420 calls selected data elements from datastore 425 appropriate to the diagnosis. The values of the selected data elements are weighted according to an algorithm and a patient severity score is determined. This patient severity score is used to determine whether the patient is treated in a patient monitoring station. For example, if one embodiment of the present invention, if the severity score is greater than or equal to a particular threshold, the patient is identified as requiring observation via a patient monitoring station. If the severity score is less than that threshold, the patient is triaged to a facility other than a patient monitoring station, thereby assigning patient monitoring stations to patients who are most likely to benefit from monitoring and continued assessment.

In another embodiment of the present invention, computer 405 operates order writing software 415, either independently or in conjunction with the operation of continued care software 420 to order tests to complete the data required for a potential diagnosis.

Figure 5:
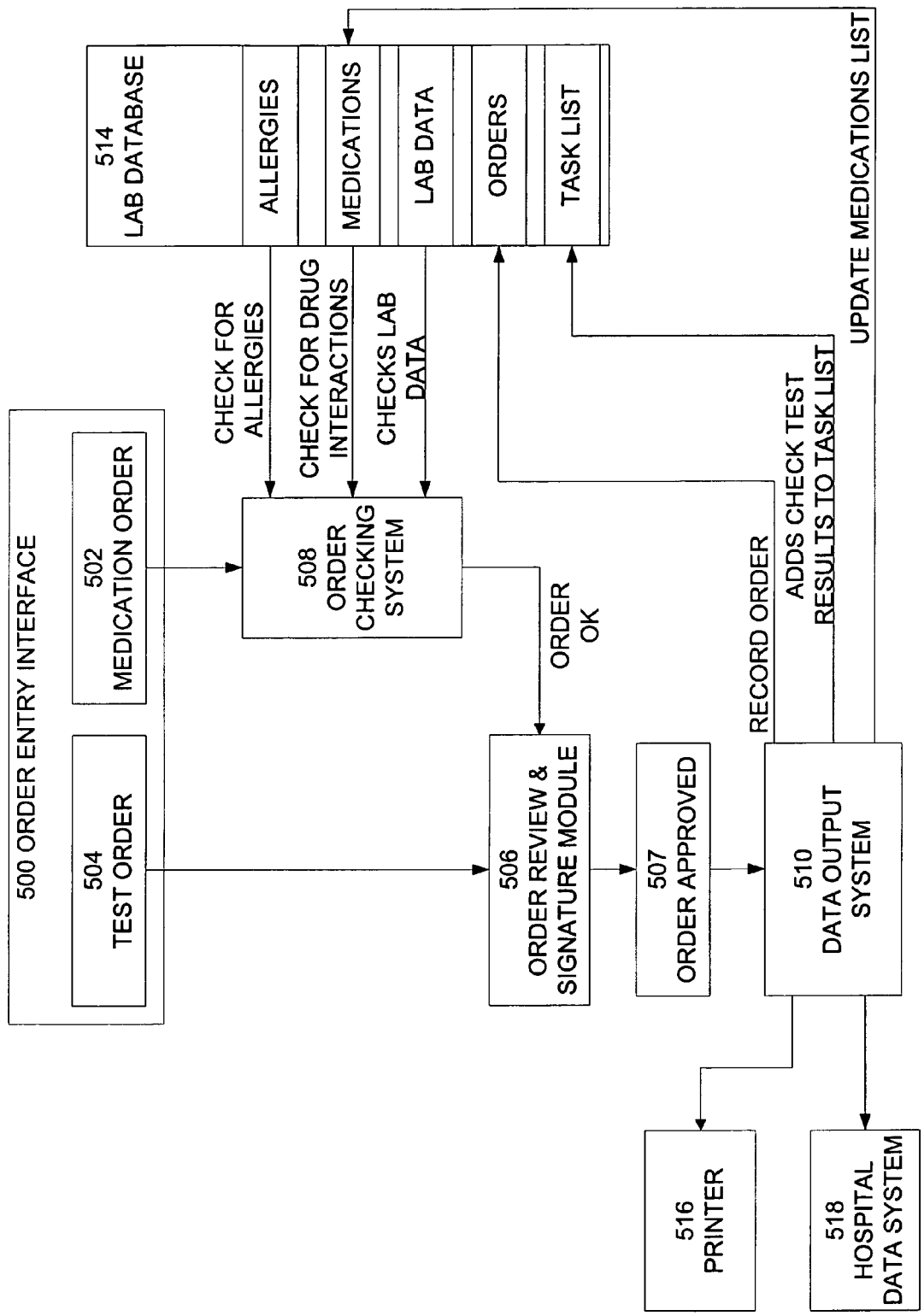
FIG. 5 illustrates an order writing data flow according to an embodiment of the present invention.

FIG. 5 illustrates an order writing data flow according to an embodiment of the present invention. Referring to FIG. 5, order entry user interface 500 allows the caregiver to order procedures and medication to assist the patients at a patient monitoring station. For example, the caregiver can order an ECG 504. Thereafter the order is reviewed and a digital signature relating to the caregiver is supplied 506. Once reviewed and signed off, the order is approved 507 and sent to the data output system 510. Thereafter the data output system prints the order to the printer at a patient monitoring station 516. For record keeping purposes the order is exported in the HL7 language to the hospital data system 518. In addition the data output system adds an item to the database that will subsequently cause a caregiver to check the ECG results. This notification to the task list is provided to the database 514. In addition, as part of the database an orders file relating to the specific patient is also kept. The fact that an ECG has been ordered is entered in the orders file for that patient.

In a similar fashion using the order entry user interface 500 the caregiver can order medications 502 for a patient. The medication order then is provided to an order checking system 508. The order checking system retrieves information from the database 514 relating to allergies of the patient and medication list that comprises medications that are already being administered to the patient. This allows for the order checking system to check for drug allergies and drug interactions. Further laboratory data is extracted from the database 514 and the order checking system checks to insure that there will be no adverse impact of the recommended dosage upon the renal function of the patient. Once the order checking system 508 is completed, the order is approved and provided to the order review and signature module 506. In this module the digital signature of a caregiver is affixed to the order electronically and the order is approved 507. Thereafter it is provided to the data output system 510 where again the orders are printed or transmitted via HL7 for the patient monitoring station 516, for the pharmacy 517 and for the treatment facility data system 518. In this case, any medications that are ordered are then provided to the medications list file in the database 514 so that the complete list of all medications that are being administered to the patient is current.

As noted, the order writing software 415 may also interact with continued care software 410. Referring again to FIG. 4, a caregiver selects a suggested diagnosis from the continued care software 420 and enters the order writing software 415. The order writing software identifies the appropriate test or tests and issues the actual order or orders for the identified tests. Each order is then sent to the appropriate testing facility. The tests are conducted, and the completion of the order is reported to the data store 425 and the completion information is received by the order writing software 415. Additionally, continued care software 420 acquires the test results from the datastore 425 and updates the list of suggested diagnoses.

Continued care software 420 provides reference material directed to the standardized treatment of the hospitalized patient. In order to standardize treatment provided to monitored hospitalized patients at the highest possible level, decision support algorithms are used in the present invention. These include textural material describing the topic, scientific treatments and possible complications. This information is available in real time to assist in all types of clinical decisions from diagnosis to treatment to triage.

As noted earlier, an aspect of the present invention is to standardize care and treatment across patient monitoring stations. This is effective in the present invention by providing decision support to caregivers as well as information concerning the latest care and practice standards for any given condition. Table 1 below is an exemplary list of a wide variety of conditions within the general categories of cardiovascular, endocrinology, general, gastrointestinal, hematology, infectious diseases, neurology, pharmacology, pulmonary, renal, surgery, toxicology, for which algorithms of care have been developed. As will be appreciated by those skilled in the art, the list in Table 1 is not exhaustive and other decision support algorithms may be developed for other conditions without departing from the scope of the present invention.

TABLE 1

Figure 6A:
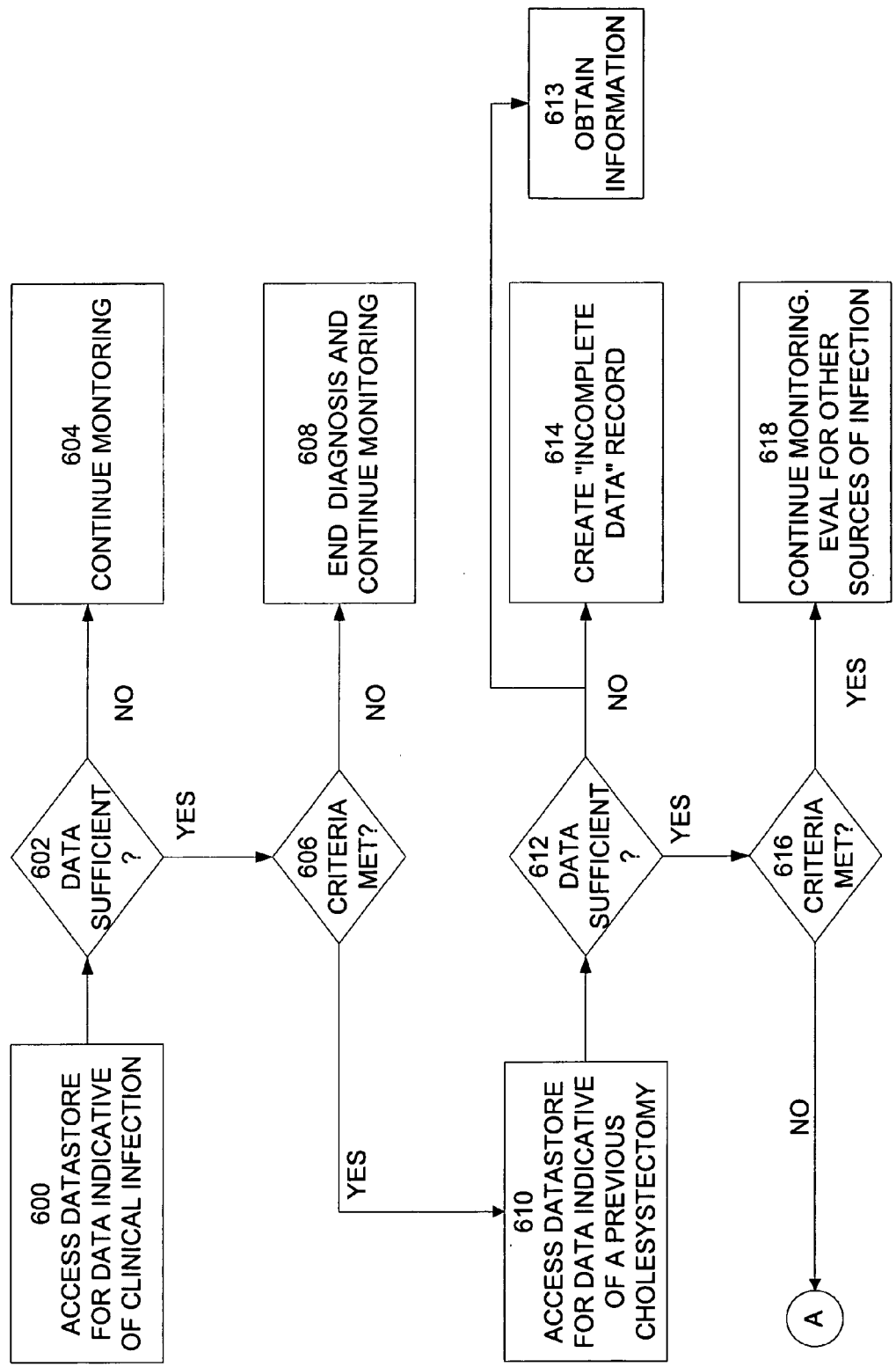
FIGS. 6A, B, C, and 6D illustrate the flow of a decision support algorithm for acalculous cholecsystitis according to an embodiment of the present invention.

Bradyarrhythmias diagnosis & treatment
Cardiogenic shock treatment
Cardio-pulmonary resuscitation treatment
Congestive heart failure diagnosis & treatment
Emergency cardiac pacing indications
Fluid resuscitation indications & treatment
Hypertensive crisis treatment
Implantable cardio-defibrillators indications
Intra-aortic balloon devices indications
Magnesium treatment
Treatment of hypotension
Myocardial infarction diagnosis & treatment
MI with left bundle branch block diagnosis
Pulmonary artery catheter indications
Permanent pacemakers indications
Pulmonary embolism diagnosis
Pulmonary embolism treatment
Supra-ventricular tachyarrhythmias diagnosis & treatments
Unstable angina diagnosis & treatment
Venous thromboembolism prophylaxis treatment
Venous thrombosis: diagnosis & treatment
Ventricular arrhythmias diagnosis & treatment
Adrenal insufficiency diagnosis and treatment
Diabetic ketoacidosis diagnosis and treatment
Hypercalcemia: diagnosis & treatment
Hyperglycemia: insulin treatment
Steroid replacement treatment
Thyroid disease diagnosis and treatment
End of life treatment decisions
Pressure ulcers treatment
Organ procurement indications
Antibiotic associated colitis diagnosis and treatment
Hepatic encephalopathy diagnosis and treatment
Hepatic failure diagnosis and treatment
Treatment of patients with ascites
Nutritional management
Acute pancreatitis diagnosis and treatment
Upper gastro-intestinal bleeding: stress prophylaxis treatment
Upper gastro-intestinal bleeding: non-variceal treatment
Upper gastro-intestinal bleeding: variceal treatment
Heparin treatment
Heparin-induced thrombocytopenia diagnosis and treatment
The bleeding patient diagnosis and treatment
Thrombocytopenia diagnosis and treatment
Thrombolytic treatment
Transfusion indications
Hematopoetic growth factor indications
Warfarin treatment
Acalculus cholecystitis diagnosis and treatment
Bloodstream infections diagnosis and treatment
Candiduria diagnosis and treatment
Catheter related septicemia diagnosis and treatment
Catheter replacement strategies
Endocarditis prophylaxis
Endocarditis diagnosis and treatment
Febrile neutropenia diagnosis and treatment
Fever of Unknown Origin diagnosis
HIV+ patient infections diagnosis and treatment
Meningitis diagnosis and treatment
Necrotizing soft tissue infections diagnosis and treatment
Non-infectious causes of fever diagnosis
Ophthalmic infections diagnosis and treatment
Pneumonia, community acquired diagnosis and treatment
Pneumonia, hospital acquired diagnosis and treatment
Septic shock diagnosis and treatment
Sinusitis diagnosis and treatment
Systemic Inflammatory Response Syndrome diagnosis TABLE 1-continued and treatment
Transplant infection prophylaxis
Transplant-related infections diagnosis and treatment
Agitation, anxiety, depression & withdrawal treatment
Brain death diagnosis
Guillain-barre syndrome diagnosis and treatment
Intracerebral hemorrhage diagnosis and treatment
Myasthenia gravis diagnosis and treatment
Neuromuscular complications of critical illness diagnosis and treatment
Non-traumatic coma diagnosis
Sedation treatment
Status epilepticus diagnosis and treatment
Stroke diagnosis and treatment
Sub-arachnoid hemorrhage diagnosis and treatment
Aminoglycoside dosing and therapeutic monitoring
Amphotericin-b treatment
Analgesia treatment
Drug changes with renal dysfunction
Penicillin allergy diagnosis and treatment
Neuromuscular blocker treatment
Vancomycin treatment
Adult Respiratory Distress Syndrome: hemodynamic treatment
Adult Respiratory Distress Syndrome: steroid treatment
Adult Respiratory Distress Syndrome: ventilator treatment
Asthma diagnosis & treatment
Bronchodilator use in ventilator patients
Bronchoscopy & thoracentesis indications
Chronic Obstructive Pulmonary Disease treatment
Chest X-ray indications
Noninvasive modes of ventilation indications
Endotracheal tubes & tracheotomy indications
Treatment of airway obstruction
Ventilator weaning
Acute renal failure: diagnosis and treatment
Dialysis indications
Diuretic treatment
Hyperkalemia: diagnosis & treatment
Hypernatremia: diagnosis & treatment
Hypokalemia: diagnosis & treatment
Hyponatremia: diagnosis & treatment
Oliguria diagnosis and treatment
Obstetrical complications and treatment
Dissecting aortic aneurysm diagnosis and treatment
Post-operative hypertension treatment
Post-operative myocardial ischemia (non-cardiac surgery) treatment
Diagnosis and treatment of arrhythmias after cardiac surgery
Diagnosis and treatment of post-operative bleeding
Post-operative management of abdominal
Post-operative management of open heart
Post-operative management of thoracotomy
Post-operative management of carotid
Wound healing treatment
Diagnosis and treatment of acetaminophen overdose
Diagnosis and treatment of anaphylaxis
Diagnosis and treatment of cocaine toxicity
Diagnosis and treatment of alcohol withdrawal
Diagnosis and treatment of hyperthermia
Diagnosis and treatment of latex allergy
Diagnosis and treatment of unknown poisoning
Diagnosis and treatment of abdominal compartment syndrome
Diagnosis and treatment of blunt abdominal injury
Diagnosis and treatment of blunt aortic injury
Diagnosis and treatment of blunt cardiac injury
Deep Venous Thrombosis prophylaxis treatments
Acid-base disturbance diagnosis and treatment
Electrolyte disturbance diagnosis and treatment
Severity adjustment calculation and outcome prediction
Ventilator treatment
Continuous renal replacement treatment
Infusion pump administration treatment
Fungal infection diagnosis and treatment
Viral infection diagnosis and treatment
Diagnosis and treatment of extremity compartment syndrome
Diagnosis and treatment of head injury
Diagnosis and treatment of hypothermia
Diagnosis and treatment of identification of cervical cord injury
Diagnosis and treatment of spinal cord injury
Diagnosis and treatment of open fractures
Diagnosis and treatment of penetrating abdominal injury
Diagnosis and treatment of penetrating chest injury
Admission criteria
Discharge criteria
Patient triage
Discharge planning FIGS. 6A, B, C and 6D illustrate an application of a decision support algorithm for the diagnosis and treatment of acalculous cholecystitis to patient data according to an embodiment of the present invention. FIGS. 6A through 6D are exemplary only and are not limiting. As will be appreciated by those skilled in the art, decision support algorithms (DSAs) for other conditions may be implemented in the continued patient care software without departing from the scope of the present invention.

Referring to FIG. 6A, a datastore comprising patient data is accessed by the DSA 600 for data indicative of clinical infection. A determination is made whether the data is sufficient to determine whether the patient is clinically infected 602. If the data necessary to make the decision are not available, the system continues its monitoring 604 until data in the datastore indicates otherwise. Alternatively, an alert may be issued on a monitor at the command center although this is not a requirement for further tests to be ordered. Test that are ordered by the DSA are then performed on the patient to obtain the data required for the decision.

If the data are sufficient, a determination is made whether the patient meets criteria for a clinical infection as measured by elevated temperature and leukocystosis 606. In an embodiment of the present invention, the criteria are temperature great than 102 F, or a white blood cell count greater than 12,000. If the criteria for clinical infection are not met the system of the present invention goes back into its continuous monitoring mode 608. The process is then complete and the continuous monitoring of the present invention continues.

If the patient is clinically infected 606, the DSA accesses the patient data datastore and acquires data indicative of whether the patient has had a previous cholecystectomy 610. A determination is then made whether the data is sufficient to determine whether the patient has had a previous cholecystectomy 612. If the data necessary to make the decision are not available, the DSA prompts the caregiver to find out this information 613. When the information is obtained it is put into the datastore. Notations of "incomplete data" are kept by the system so that treatment records and need for tests can be audited. This is accomplished by storing an "incomplete data" record 614.

If the data are sufficient, a determination is made whether the patient has had a previous cholecystectomy 616. If the patient has had a previous cholecystectomy, it is very unlikely that the patient has acalculous cholecystitis. Therefore the DSA has completed its analysis for acalculous cholecytitis and the continuous monitoring of the present invention continues for other possible etiologies of infection 618.

Figure 6B:
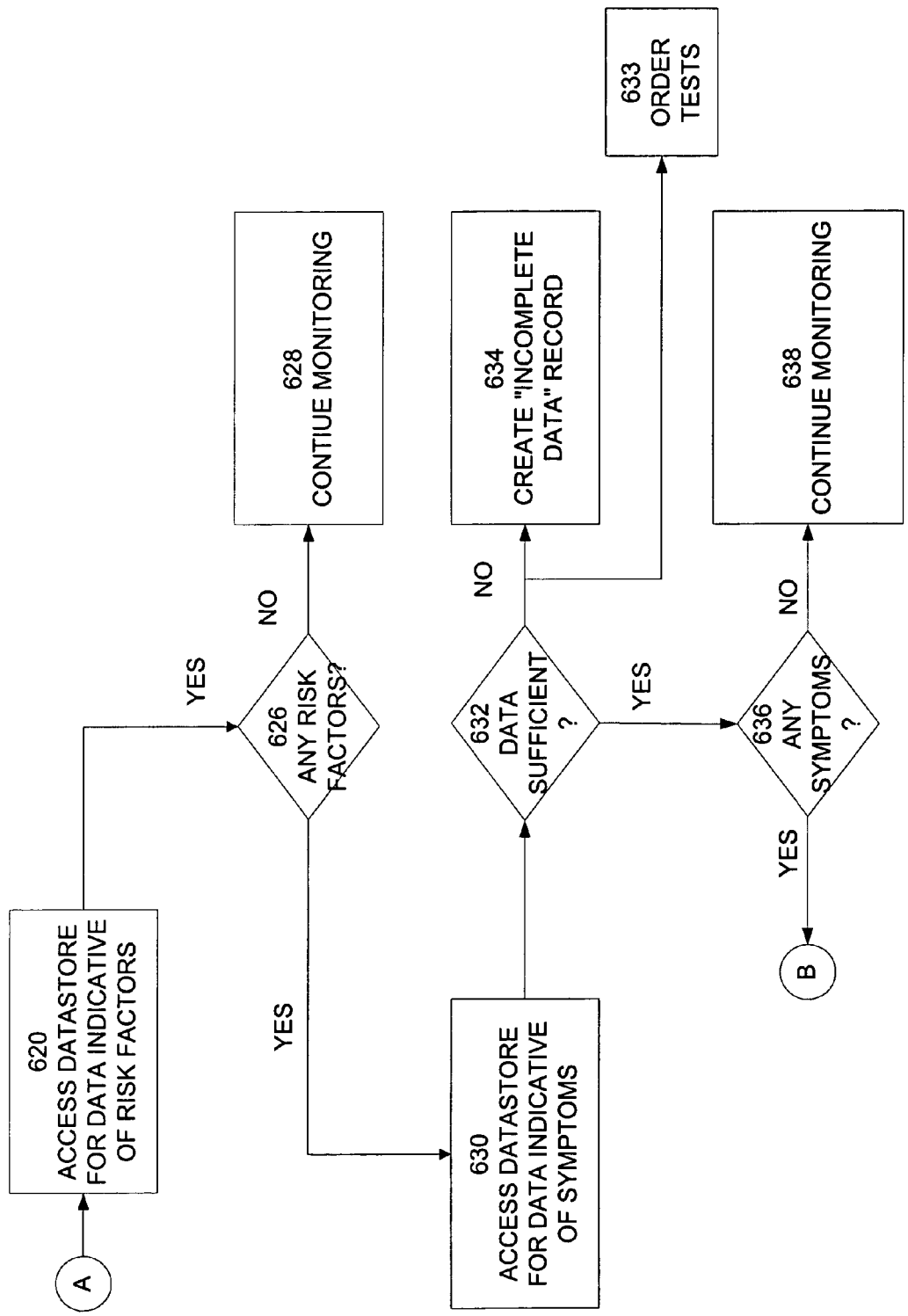

Referring to FIG. 6B, if the patient has not had a previous cholecystectomy, the DSA accesses the patient datastore and acquires data indicative of whether the patient has any of a set of risk factors 620. In another embodiment of the present invention, the risk factors comprise: 1) Prolonged intensive care unit (ICU) stay (defined as greater than six (6) days); 2) recent surgery within the last two weeks (particularly aortic cross clamp procedures); 3) hypotension (BP less than 90 mmHg); 4) positive end-expiratory pressure (PEEP) greater than ten (10) centimeters (cm); 5) transfusion greater than six (6) units of blood; 6) inability to use the gastrointestinal (GI) tract for nutrition; or 7) immunosuppression (AIDS, transplantation, or leukemia).

If the data are sufficient, a determination is made whether the patient has any of the risk factors 626. If the patient does not have any of the risk factors, the diagnostic process is then complete and the continuous monitoring of the present invention continues 628.

If the patient has any of the seven risk factors, the DSA accesses the patient data datastore and acquires data indicative of whether the patient has any of a set of symptoms 630 or abnormal laboratory values. A determination is made whether the data is sufficient to determine whether the patient has any of the symptoms 632 or abnormal laboratory values. If the data necessary to make the decision are not available, the DSA directs the order writing software 415 (see FIG. 4) to order the tests 633. Results are sent to the datastore. Notations of "incomplete data" are kept by the system so that treatment records and need for tests can be audited. This is accomplished by storing an "incomplete data" record 634. Alternatively, an alert may be issued on a monitor at the command center to check for right upper quadrant tenderness although this is not a requirement for further tests to be ordered. In another embodiment of the present invention, the symptoms comprise: right upper quadrant (RUQ) tenderness and the abnormal laboratory results comprising elevated alkaline phosphatase; elevated bilirubin; or elevated liver transaminases.

If the data are sufficient, a determination is made whether the patient has any of the symptoms 636 or abnormal laboratory values. If the patient does not have any of the symptoms or abnormal laboratory values, the DSA concludes that it is very unlikely that the patient has acalculous cholecystitis. The process is then complete and the continuous monitoring of the present invention continues 638.

Referring to FIG. 6C, if the patient has any of the symptoms or abnormal laboratory values, the DSA accesses the patient data datastore and acquires data indicative of whether alternative intra-abdominal infectious sources are more likely 640. A determination is made whether the data is sufficient to determine whether the other infectious sources are more likely 642. If the data necessary to make the decision are not available, the DSA prompts the user for a response as to whether other infectious causes are present and considered more likely 644. The user can then provide the requested information that can be considered by the system 646 for further analysis.

If the data are sufficient, a determination is made whether other sources of infection are more likely 646. Regardless of the outcome of this determination, the DSA accesses the patient datastore and acquires data indicative of whether the patient is sufficiently stable to be subjected to testing outside of the critical care environment 650. A determination is made whether the data are sufficient to determine whether the patient is stable to go outside of the critical care environment 652. If the data necessary to make the decision are not available, the DSA prompts the user for a response 654 and may direct the order writing software 415 (see FIG. 4) to order tests or procedures 653 that will assist in such a determination. An "incomplete data" record is also created 651. Test results are sent to the datastore. Notations of "incomplete data" are kept by the system so that treatment records and need for tests can be audited. This is accomplished by storing an "incomplete data" record 654. Alternatively, an alert may be issued on a monitor at the command center although this is not a requirement for further tests to be ordered.

Figure 6D:
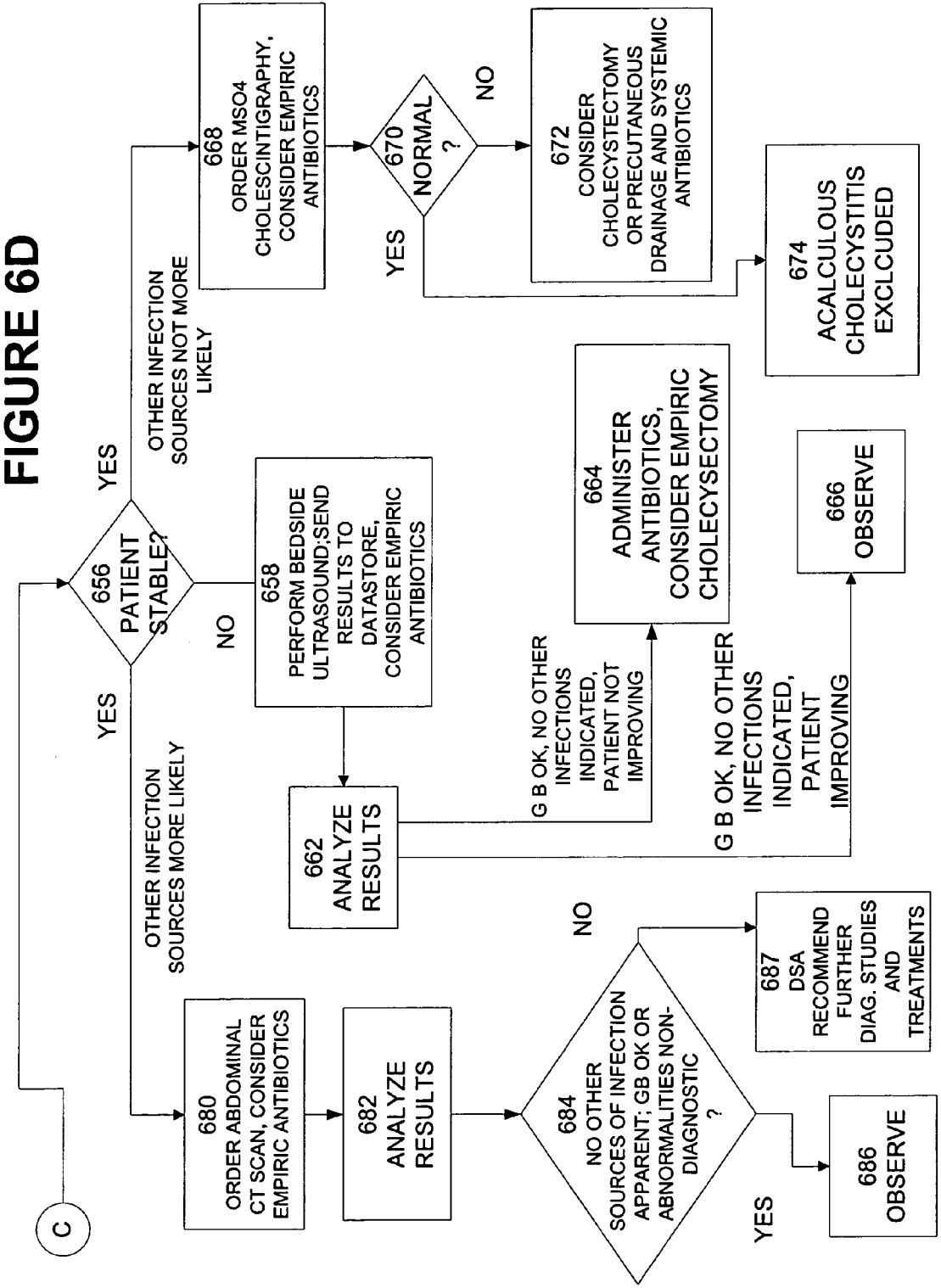

Referring to FIG. 6D, if the data are sufficient, a determination is made whether the patient is sufficiently stable to be subjected to testing outside of the critical care environment 656.

If the patient is not sufficiently stable to be subjected to testing outside of the critical care environment (regardless of whether other sources of infection are indicated), the DSA issues a message comprising a recommendation that empiric antibiotic be considered and a bedside ultrasound be performed and the results communicated to the patient datastore 658. In still another embodiment of the present invention, the DSA directs the order writing software (see FIG. 4) to order the bedside ultrasound. The DSA accesses the test results and other patient data 662. If no other infectious etiologies are identified, no abnormalities of the gall-bladder are noted, and the patient is not improving, the DSA issues a message comprising a "provisional diagnosis of acalculous cholecystitis" and recommends an empiric cholecystectomy and systemic antibiotics 664. If no other infectious etiologies are identified, no abnormalities of the gall bladder are noted, and the patient is improving, the DSA issues a message comprising a recommendation to observe the patient 666.

If the patient is sufficiently stable to go outside of the critical care environment for a test and a determination was made that no other sources of infection were indicated (see FIG. 6C, 646), the DSA issues an order that empiric antibiotics be considered and a morphine sulfate Cholescintigraphy test be performed 668 and the results communicated to the datastore. In still another embodiment of the present invention, the DSA directs the order writing software 415 (see FIG. 4) to order the test.

A determination is made whether the results of the tests are normal 670. If the test indicates an abnormality, the DSA issues a message comprising a recommendation to consider a diagnosis of acalculous cholecystitis, administer systemic antibiotics and perform either a cholecystectomy or a percutaneous drainage 672. If the results are normal, acalculous cholecystitis is excluded 674. The process is then complete and the continuous monitoring of the present invention continues.

If the patient is sufficiently stable to go outside of the critical care environment for a test and a determination was made that other sources of infection were indicated (see FIG. 6C, 646), the DSA issues an order to consider empiric antibiotics and for an abdominal CT scan to be performed 680 and the results communicated to the datastore. In still another embodiment of the present invention, the DSA directs the order writing software 415 (see FIG. 4) to order the test.

The test results and other data are analyzed 682 and a determination is made whether other infection sources are indicated and whether the gall bladder is normal or if abnormalities are present that are not diagnostic 684. If other infectious etiologies are not apparent and the test: a) demonstrates abnormalities of the gall bladder but not diagnostic; or b) no gall-bladder abnormalities are noted, the DSA issues a report comprising a recommendation to maintain continued observation of the patient 686. The process is then complete and the continuous monitoring of the present invention continues. Alternatively, if other infectious etiologies are apparent, the DSA will make recommendations as to further diagnostics and treatments.

Referring again to FIGS. 1 and 2, the remote command center comprises an A/V conferencing server 190. In an embodiment of the present invention, A/V conferencing server 190 acquires audio and video signals from patient monitoring station "A" and provides a terminal (not shown) access to these signals via external network access 195. In yet another embodiment of the present invention addition, a local terminal (not shown) operated by a "local visitation participant" or "LVP" and a remote terminal (not shown) operated by a "remote visitation participant" or "RVP" are bridged by A/V conferencing server 190 to provide audio and video signals from the patient monitoring station, the local terminal and the remote terminal available simultaneously to LVP and RVP. Additionally, a terminal user may control the position of camera 205. By way of illustration and not as a limitation, RVPs may be family members or other concerned parties while LVPs may be patients, nurses, doctors, family members or other concerned parties. This embodiment thus permits family members the capability to "virtually visit" other sick family members when a physical visit to a patient's location is not possible and/or desirable. The "virtual visit" further allows the possibility to see and speak with a care provider regarding a patient's care or related subjects without having to be physically located at the health care provider's location. The present invention also provides a means for the floor staff (i.e. those caregivers in the hospital at or near the patient's bedside) to instantly alert the command center of the conditions of patients who destabilize thereby allowing for more rapid response by those manning the command center.

When each command center person logs onto the system of the present invention, a background service is started. This service subscribes to an emergency alert server that is connected to a video server. As noted earlier, the video server provides video feed from each beside to the command center as needed. Emergency message are passed from the bedside through the video server to the command center. As the emergency alert server receives a message from a video server, it sends a message to all of the subscribed services in the command center. This notification alerts the command center users by means of a "pop-up" alert window at the users' workstation that an emergency condition exists at the bed calling for the alert, and that the floor caregiver has requested immediate backup.

To facilitate the emergency call capability of the present invention, in addition to the various network connections of a more automated type, an emergency "call button" is provided at each critical care location. This could by or near each bed, at a nurse's station, at a mobile care bed or any location where the patient may be located. When pressed, the call button causes a message to be sent to the emergency alert server at the command center that a patient emergency has occurred.

The present invention comprises a video/audio server (Axis 2401) dedicated to each critical care location. A button activation mechanism and associated wiring is provided to allow the call button to be positioned in the room at a location convenient to the caregiver calling for command center backup.

Currently each video server can support up to 16 call buttons by using combinations of the four inputs to signify one alarm in a 4-bit binary pattern although this is not meant as a limitation. A typical installation would use one button or perhaps two (e.g. two beds per room) per video server.

A software interrupt event handler is configured on the video server to respond to activation of the emergency call button.

The emergency alert server comprises a web service called for sending emergency alert signals that is placed in service at system startup. When called, emergency alert web service responds with an acknowledgement message (e.g. "Alert Received"). The emergency alert web service identifies the ward and bed directly from the IP address (unique to each video server) and input number it was passed. It then sends a message to all subscribing clients identifying the emergency condition, the ward, and bed.

When a user logs into a workstation at the command center a user alert service subscribes to the emergency alert server and waits for any emergency message in the background. Upon receiving an emergency message, the service will popup a window with the message on top of the desktop and stay there until the user dismisses or acknowledges the alert. The user alert service the loads video assessment module to allow the command center to view the bed with the emergency.

In another embodiment of the present invention, a critical care hospital bed comprises monitoring instruments linked to a wireless network. This serves the needs of those patients who are transported from one location to another (either internal to a hospital or to other hospitals or diagnostic centers) for testing, procedures or other reasons. In this embodiment, monitoring continues using typical monitoring means that have been described above which include, without limitation, physiological monitoring equipment, video monitoring equipment and an emergency call button, all of which transmit their signals in a wireless fashion so that movement of the patient bed does not interrupt the transmission of information.

A telecommunications network for remote patient monitoring has now been illustrated. It will be apparent to those skilled in the art that other variations of the present invention are possible without departing from the scope of the invention as disclosed. For example, one can envision different ratios of remote command center to patient monitoring stations. Certain types of decision support algorithms would be used by intensivists, other types of remote monitoring of not only patient monitoring stations but other types of hospital functions as well as industrial functions where critical expertise is in limited supply but where that expertise must be applied to ongoing processes. In such cases a system such as that described can be employed to monitor processes and to provide standardized interventions across a number of geographically dispersed locations and operations. Further, any reference to claim elements in the singular, for example, using the articles "a," "an," or "the" is not to be construed as limiting the element to the singular.

What is claimed is:

1. A hospitalized patient care system comprising:
   a telecommunication network;
   monitoring stations comprising monitoring equipment adapted to monitor data elements from geographically dispersed hospitalized patients and to send the monitored data elements to a remote command center via the telecommunications network, wherein the remote command center is adapted to:
   receive the monitored data elements from the geographically dispersed hospitalized patients;
   access patient data elements indicative of a medical condition associated with each of the geographically dispersed hospitalized patients;

establish patient-specific rules associated with each of the geographically dispersed hospitalized patients; and apply the patient-specific rules continuously and simultaneously using a rules engine adapted to:
  select data elements from the monitored data elements and the patient data elements associated with a hospitalized patient;
  apply a patient-specific rule associated with the hospitalized patient to the selected data elements;
  determine in an automated fashion at the remote command center whether the patient-specific rule for the hospitalized patient has been contravened; and
  in the event the patient-specific rule for the hospitalized patient has been contravened, issue an alert from the remote command center.

2. The system of claim 1, wherein the patient specific rule for the hospitalized patient comprises an algorithm.

3. The system of claim 1, wherein the selected data elements comprise a physiological data element of the hospitalized patient and a clinical data element of the hospitalized patient.

4. The system of claim 1, wherein the selected data elements comprise a physiological data element of the hospitalized patient and a medication data element of the hospitalized patient.

5. The system of claim 1, wherein the selected data elements comprise a physiological data element of the hospitalized patient and a laboratory data element of the hospitalized patient.

6. The system of claim 1, wherein the selected data elements comprise a clinical data element of the hospitalized patient and a laboratory data element of the hospitalized patient.

7. The system of claim 1, wherein the selected data elements comprise a physiological data element of the hospitalized patient and another physiological data element of the hospitalized patient.

8. The system of claim 1, wherein the selected data elements comprise at least two data elements of the hospitalized patient selected from the group consisting of a physiological data element, a clinical data element of the hospitalized patient, a medication data element of the hospitalized patient, and a laboratory data element of the hospitalized patient.

9. The system of claim 1, wherein the alert comprises a patient intervention protocol and order.

10. The system of claim 1 wherein the rules engine is further adapted to:
  determine whether the hospitalized patient requires monitoring by the monitoring station; and
  in the event the hospitalized patient does not require monitoring by the monitoring station, issue a release protocol and order.

11. The system of claim 1, wherein monitoring equipment further comprises physiological sensors and monitored data elements comprise physiological data elements.

12. The system of claim 1, wherein monitoring equipment further comprises:
  a video imaging system and wherein monitored data elements comprises video image data elements, and
  a voice communication system and wherein monitored data further comprises audio data elements.

13. The system of claim 12, wherein the hospitalized patient care system further comprises an audio/video teleconferencing server, and wherein the audio/video teleconferencing server is adapted to:
  bridge a local visitation terminal and a remote visitation terminal;
  send audio and video signals generated by the local visitation terminal to the remote visitation terminal;
  send audio and video signals generated by the remote visitation terminal to the local visitation terminal; and
  provide the audio data elements and video image data elements to both the remote visitation terminal and the local visitation terminal.

14. The system of claim 1, wherein the hospitalized patient care system further comprises a patient support system adapted to:
  access a decision support algorithm;
  apply the decision support algorithm to selected data elements of a hospitalized patient;
  apply the decision support algorithm to user input; and
  provide patient care advice to the user.

15. The system of claim 14, wherein the patient care advice is a diagnosis.

16. The system of claim 14, wherein the patient care advice is a method of treatment.

17. The system of claim 14, wherein the patient care advice is a laboratory protocol.

18. The system of claim 14, wherein the patient support system is further adapted to:
  access an order writing module; and
  issue an order.

19. The system of claim 18, wherein the order comprises authorization to administer medication to the hospitalized patient.

20. The system of claim 18, wherein the order comprises authorization to subject the hospitalized patient to a laboratory protocol.

21. The system of claim 18, wherein the order comprises authorization to subject the hospitalized patient to a surgical procedure.

22. A method for continuous assessment of geographically dispersed hospitalized patients:
  receiving at a remote command center monitored data elements from geographically dispersed hospitalized patients via a telecommunications network;
  accessing patient data elements indicative of a medical condition associated with each of the geographically dispersed hospitalized patients;
  establishing patient-specific rules associated with each of the geographically dispersed hospitalized patients;
  selecting data elements from the monitored data elements and the patient data elements associated with a hospitalized patient;
  applying a patient-specific rule associated with the hospitalized patient to the selected data elements;
  making a determination in an automated fashion at the remote command center whether the patient-specific rule for the hospitalized patient has been contravened; and
  in the event the patient-specific rule for the hospitalized patient has been contravened, issuing an alert from the remote command center.

23. The method for continuous assessment of geographically dispersed hospitalized patients as in claim 22, wherein selecting data elements from the monitored data elements associated with a hospitalized patient and the patient data elements associated with a hospitalized patient comprises selecting a physiological data element of the hospitalized patient and a clinical data element of the hospitalized patient.

24. The method for continuous assessment of geographically dispersed hospitalized patients as in claim 22, wherein selecting data elements from the monitored data elements associated with a hospitalized patient and the patient data elements associated with a hospitalized patient comprises selecting a physiological data element and a medication data element of the hospitalized patient.

25. The method for continuous assessment of geographically dispersed hospitalized patients as in claim 22, wherein selecting data elements from the monitored data elements associated with a hospitalized patient and the patient data elements associated with a hospitalized patient comprises selecting a physiological data element of the hospitalized patient and a laboratory data element of the hospitalized patient.

26. The method for continuous assessment of geographically dispersed hospitalized patients as in claim 22, wherein selecting data elements from the monitored data elements associated with a hospitalized patient and the patient data elements associated with a hospitalized patient comprises selecting a clinical data element of the hospitalized patient and a laboratory data element of the hospitalized patient.

27. The method for continuous assessment of geographically dispersed hospitalized patients as in claim 22, wherein selecting data elements from the monitored data elements associated with a hospitalized patient and the patient data elements associated with a hospitalized patient comprises selecting a physiological data element of the hospitalized patient and another physiological data element of the hospitalized patient.

28. The method for continuous assessment of geographically dispersed hospitalized patients as in claim 22, wherein selecting data elements from the monitored data elements associated with a hospitalized patient and the patient data elements associated with a hospitalized patient comprises selecting at least two data elements of the hospitalized patient selected from the group consisting of a physiological data element, a clinical data element of the hospitalized patient, a medication data element of the hospitalized patient, and a laboratory data element of the hospitalized patient.

29. The method for continuous assessment of geographically dispersed hospitalized patients as in claim 22, wherein issuing an alert comprises issuing a patient intervention protocol and order.

30. The method for continuous assessment of geographically dispersed hospitalized patients as in claim 22, further comprising:
making a determination whether the hospitalized patient requires monitoring; and
in the event the hospitalized patient does not require monitoring, issuing a release protocol and order.

31. The method for continuous assessment of geographically dispersed hospitalized patients as in claim 22, wherein receiving at a remote command center monitored data elements from geographically dispersed hospitalized patients comprises receiving physiological data elements.

32. The method for continuous assessment of geographically dispersed hospitalized patients as in claim 22, wherein receiving at a remote command center monitored data elements from geographically dispersed hospitalized patients comprises receiving video image data elements and audio data elements.

33. The method for continuous assessment of geographically dispersed hospitalized patients as in claim 32, wherein the method further comprises:
bridging a local visitation terminal and a remote visitation terminal;
sending audio and video signals generated by the local visitation terminal to the remote visitation terminal;
sending audio and video signals generated by the remote visitation terminal to the local visitation terminal; and
providing the audio data elements and video image data elements to both the remote visitation terminal and the local visitation terminal.

34. The method for continuous assessment of geographically dispersed hospitalized patients as in claim 22, further comprising:
accessing a decision support algorithm;
applying the decision support algorithm to selected data elements of a hospitalized patient;
applying the decision support algorithm to user input; and
providing patient care advice to the user.

35. The method for continuous assessment of geographically dispersed hospitalized patients as in claim 34, wherein providing patient care advice to the user comprises providing the user a diagnosis.

36. The method for continuous assessment of geographically dispersed hospitalized patients as in claim 34, wherein providing patient care advice to the user comprises providing the user a method of treatment.

37. The method for continuous assessment of geographically dispersed hospitalized patients as in claim 34, wherein providing patient care advice to the user comprises providing the user a laboratory protocol.

38. The method for continuous assessment of geographically dispersed hospitalized patients as in claim 34, wherein the method further comprises:
accessing an order writing module; and
issuing an order.

39. The method for continuous assessment of geographically dispersed hospitalized patients as in claim 38, wherein issuing an order comprises issuing an authorization to administer medication to the hospitalized patient.

40. The method for continuous assessment of geographically dispersed hospitalized patients as in claim 38, wherein issuing an order comprises issuing an authorization to subject the hospitalized patient to a laboratory protocol.

41. The method for continuous assessment of geographically dispersed hospitalized patients as in claim 38, wherein issuing an order comprises issuing an authorization to subject the hospitalized patient to a surgical procedure.

42. The system of claim 1, wherein a monitoring station is a transportable monitoring station comprising the monitoring equipment.

43. The system of claim 42, wherein the transportable monitoring station comprises a cart.

44. The system of claim 43, wherein the transportable monitoring station further comprises a video camera, a microphone, a speaker, patient monitoring devices, a printer, a network interface, and a data entry device.

45. The system of claim 42, wherein the transportable monitoring station is wearable by the patient.

46. The system of claim 1, wherein the monitoring equipment is integrated into a patient support device.

47. The system of claim 46, wherein the patient support device is selected from the group consisting of a bed, a chair, a recliner, and a wheelchair.

48. The system of claim 1, wherein the telecommunications network comprises a wireless sub-network and wherein a monitoring station is adapted to send the monitored data elements to the remote command center via the telecommunications network using the wireless subnetwork.

49. The system of claim 48, wherein the monitoring station is a transportable monitoring station comprising the monitoring equipment.

50. The system of claim 49, wherein the transportable monitoring station comprises a cart.

51. The system of claim 50, wherein the transportable monitoring station further comprises a video camera, a microphone, a speaker, patient monitoring devices, a printer, a network interface, and a data entry device.

52. The system of claim 49, the transportable monitoring station is wearable by the patient.

53. The system of claim 48, wherein the monitoring equipment is integrated into a patient support device.

54. The system of claim 53, wherein the patient support device is selected from the group consisting of a bed, a chair, a recliner, and a wheelchair.

55. The system of claim 1, wherein the hospitalized patient is located in a hospital.

56. The system of claim 1, wherein the hospitalized patient is located in a nursing home.

57. The system of claim 1, wherein the hospitalized patient is located in a mobile health care facility.

58. The system of claim 57, wherein the mobile health care facility is selected from the group consisting of a ship, a helicopter, and an ambulance.

59. The system of claim 1, wherein the hospitalized patient is located in a space-based health care facility.

60. The system of claim 1, wherein the hospitalized patient is located in a field health care facility.

61. The system of claim 1, wherein the hospitalized patient is located in a residence.

62. The system of claim 1, wherein the wherein the hospitalized patient is located in an emergency room.

63. The system of claim 1, wherein the wherein the hospitalized patient is located in an intensive care unit.

64. The system of claim 1, wherein the wherein the hospitalized patient is located in an operating room.

65. The system of claim 1, wherein the wherein the hospitalized patient is located in a step down unit.

66. The method for continuous assessment of geographically dispersed hospitalized patients as in claim 22, wherein the monitored data elements are acquired using a transportable monitoring station.

67. The method for continuous assessment of geographically dispersed hospitalized patients as in claim 66, wherein the transportable monitoring station comprises a cart.

68. The method for continuous assessment of geographically dispersed hospitalized patients as in claim 67, wherein the transportable monitoring station further comprises a video camera, a microphone, a speaker, patient monitoring devices, a printer, a network interface, and a data entry device.

69. The method for continuous assessment of geographically dispersed hospitalized patients as in claim 67, wherein the transportable monitoring station is wearable by the patient.

70. The method for continuous assessment of geographically dispersed hospitalized patients as in claim 22, wherein the monitored data elements are acquired using monitoring equipment integrated into a patient support device.

71. The method for continuous assessment of geographically dispersed hospitalized patients as in claim 70, wherein the patient support device is selected from the group consisting of a bed, a chair, a recliner, and a wheelchair.

72. The method for continuous assessment of geographically dispersed hospitalized patients as in claim 22, wherein the telecommunications network comprises a wireless subnetwork and wherein receiving at a remote command center monitored data elements from geographically dispersed hospitalized patients via a telecommunications network comprises receiving at the remote command center monitored data elements from the geographically dispersed hospitalized patients via the wireless subnetwork.

73. The method for continuous assessment of geographically dispersed hospitalized patients as in claim 72, wherein the monitored data elements are acquired using a transportable monitoring station comprising monitoring equipment.

74. The method for continuous assessment of geographically dispersed hospitalized patients as in claim 73, wherein the transportable monitoring station comprises a cart.

75. The method for continuous assessment of geographically dispersed hospitalized patients as in claim 74, wherein the transportable monitoring station further comprises a video camera, a microphone, a speaker, patient monitoring devices, a printer, a network interface, and a data entry device.

76. The method for continuous assessment of geographically dispersed hospitalized patients as in claim 73, wherein the transportable monitoring station is wearable by the patient.

77. The method for continuous assessment of geographically dispersed hospitalized patients as in claim 72, wherein the monitored data elements are acquired using monitoring equipment integrated into a patient support device.

78. The method for continuous assessment of geographically dispersed hospitalized patients as in claim 77, wherein the patient support device is selected from the group consisting of a bed, a chair, a recliner, a wheelchair, a stretcher and a gurney.

79. The method for continuous assessment of geographically dispersed hospitalized patients as in claim 22, wherein the hospitalized patient is located in a hospital.

80. The method for continuous assessment of geographically dispersed hospitalized patients as in claim 22, wherein the hospitalized patient is located in a nursing home.

81. The method for continuous assessment of geographically dispersed hospitalized patients as in claim 22, wherein the hospitalized patient is located in mobile health care facility.

82. The method for continuous assessment of geographically dispersed hospitalized patients as in claim 81, wherein the mobile health care facility is selected from the group consisting of a ship, a helicopter, and an ambulance.

83. The method for continuous assessment of geographically dispersed hospitalized patients as in claim 22, wherein the hospitalized patient is located in a space-based health care facility.

84. The method for continuous assessment of geographically dispersed hospitalized patients as in claim 22, wherein the hospitalized patient is located in a field health care facility.

85. The method for continuous assessment of geographically dispersed hospitalized patients as in claim 22, wherein the hospitalized patient is located in a residence.

86. The method for continuous assessment of geographically dispersed hospitalized patients as in claim 22, wherein the wherein the hospitalized patient is located in an emergency room.

87. The method for continuous assessment of geographically dispersed hospitalized patients as in claim 22, wherein the wherein the hospitalized patient is located in an intensive care unit.

88. The method for continuous assessment of geographically dispersed hospitalized patients as in claim 22, wherein the wherein the hospitalized patient is located in an operating room.

89. The method for continuous assessment of geographically dispersed hospitalized patients as in claim 22, wherein the wherein the hospitalized patient is located in a step down unit.

* * * * *